United States Patent
Knipe et al.

(10) Patent No.: US 10,294,480 B2
(45) Date of Patent: May 21, 2019

(54) FOREIGN DNA SURVEILLANCE PROTEIN

(71) Applicant: President and Fellows of Harvard College, Cambridge, MA (US)

(72) Inventors: David M. Knipe, Auburndale, MA (US); Megan Horn Orzalli, Brookline, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 14/888,853

(22) PCT Filed: May 5, 2014

(86) PCT No.: PCT/US2014/036835
§ 371 (c)(1),
(2) Date: Nov. 3, 2015

(87) PCT Pub. No.: WO2014/179807
PCT Pub. Date: Nov. 6, 2014

(65) Prior Publication Data
US 2016/0076041 A1    Mar. 17, 2016

Related U.S. Application Data

(60) Provisional application No. 61/819,073, filed on May 3, 2013.

(51) Int. Cl.
| | | |
|---|---|---|
| A61K 48/00 | (2006.01) | |
| C12N 15/63 | (2006.01) | |
| C12N 15/11 | (2006.01) | |
| C12N 15/113 | (2010.01) | |
| G01N 33/50 | (2006.01) | |

(52) U.S. Cl.
CPC ........ *C12N 15/635* (2013.01); *A61K 48/0083* (2013.01); *C12N 15/111* (2013.01); *C12N 15/113* (2013.01); *G01N 33/5023* (2013.01); *C12N 2310/14* (2013.01); *C12N 2310/531* (2013.01)

(58) Field of Classification Search
CPC .................................................... A61K 48/00
See application file for complete search history.

(56) References Cited

U.S. PATENT DOCUMENTS 8,992,930 B2 * 3/2015 Mondini .......... C07K 16/24
                                                    424/130.1
2004/0005644 A1  1/2004 Su et al.
2005/0255487 A1 11/2005 Khvorova et al.
2013/0039933 A1  2/2013 Barber
2013/0058956 A1  3/2013 Mondini et al.

FOREIGN PATENT DOCUMENTS

JP    2012170335 A    9/2012
WO    WO-2008/028251 A1    3/2008

OTHER PUBLICATIONS

Kwak et al., (JBC 2002; vol. 278, No. 42: 40899-40904).*
Song et al., (PLoS One, Jan. 2010:(5) e8569).*
Johnstone et al., (The human interferon-inducible protein, IFI 16, is a repressor of transcription Journal J. Biol. Chem. 273 (27), 17172-17177 (1998).*
Vannucci et al., (New Micorbilogica, 36, 1-22 2013).*
Song et al., Interferon-inducible IFI16, a negative regulator of cell growth, down-regulates; expression of human telomerase reverse transcriptase (hTERT) gene. PLoS One. Jan. 5, 2010;5(1):e8569.
Cristea et al., Human cytomegalovirus pUL83 stimulates activity of the viral immediate-early promoter through its interaction with the cellular IFI16 protein. J Virol. Aug. 2010;84(15):7803-14.
Jin et al., Structures of the HIN domain:DNA complexes reveal ligand binding and activation mechanisms of the AIM2 inflammasome and IFI16 receptor. Immunity. Apr. 20, 2012;36(4):561-71.
Cai et al., Herpes simplex virus type 1 ICP0 plays a critical role in the de novo synthesis of infectious virus following transfection of viral DNA. J Virol. Nov. 1989;63(11):4579-89.
Conrady et al., Resistance to HSV-1 infection in the epithelium resides with the novel innate sensor, IFI-16. Mucosal Immunol. Mar. 2012;5(2):173-83.
Gariano et al., The intracellular DNA sensor IFI16 gene acts as restriction factor for human cytomegalovirus replication. PLoS Pathog. Jan. 2012;8(1):e1002498.
GenBank Accession No. M63838.1.
GenBank Accession No. NM_005531.2.
GenBank Accession No. NM_008329.2.
Gugliesi et al., The proapoptotic activity of the Interferon-inducible gene IFI16 provides new insights into its etiopathogenetic role in autoimmunity. J Autoimmun. Sep. 2010;35(2):114-23.
Johnson et al., Herpes simplex virus 1 infection induces activation and subsequent inhibition of the IFI16 and NLRP3 inflammasomes. J Virol. May 2013;87(9):5005-18.
Karyala et al., Translational up-regulation and high-level protein expression from plasmid vectors by mTOR activation via different pathways in PC3 and 293T cells. PLoS One. Dec. 28, 2010;5(12):e14408.
Kerur et al., IFI16 acts as a nuclear pathogen sensor to induce the inflammasome in response to Kaposi Sarcoma-associated herpesvirus infection. Cell Host Microbe. May 19, 2011;9(5):363-75.
Kumar et al., Antisense RNA: function and fate of duplex RNA in cells of higher eukaryotes. Microbiol Mol Biol Rev. Dec. 1998;62(4):1415-34.
Kwak et al., IFI16 as a negative regulator in the regulation of p53 and p21(Waf1). J Biol Chem. Oct. 17, 2003;278(42):40899-904.
Orzalli et al., Nuclear IFI16 induction of IRF-3 signaling during herpesviral infection and degradation of IFI16 by the viral ICP0 protein. Proc Natl Acad Sci U S A. Oct. 30, 2012;109(44):E3008-17.

(Continued)

*Primary Examiner* — Kimberly Chong
(74) *Attorney, Agent, or Firm* — Nixon Peabody LLP; David S. Resnick

(57) ABSTRACT

A method for augmenting expression of a heterologous nucleic acid in a eukaryotic cell or increasing the efficiency of gene expression using any gene expression system is carried out by decreasing expression or activity of an endogenous Interferon-induced protein-16 (IFI16).

24 Claims, 17 Drawing Sheets

Specification includes a Sequence Listing.

(56) References Cited

OTHER PUBLICATIONS

Orzalli et al., Nuclear interferon-inducible protein 16 promotes silencing of herpesviral and transfected DNA. Proc Natl Acad Sci U S A. Nov. 19, 2013;110(47):E4492-501.
Santa Cruz Biotechnology. IfI-16 shRNA Plasmid (h):sc-35633-SH. <http://datasheets.scbt.com/sc-35633.pdf>.
Kim et al., "IFI16 is an essential mediator of growth inhibition, but not differentiation, induced by the leukemia inhibitory factor/JAK/STAT pathway in medullary thyroid carcinoma cells" Journal of Biological Chemistry 280(6):4913-4920 (2005).

* cited by examiner

FOREIGN DNA SURVEILLANCE PROTEIN

RELATED APPLICATIONS

This application is a national stage application filed under 35 U.S.C. § 371, of International Application No. PCT/US2014/036835, filed May 5, 2014, which claims the benefit of priority under 35 U.S.C. § 119(e) to U.S. Provisional Patent Application No. 61/819,073, filed May 3, 2013, the contents of each of which are hereby incorporated by reference in their entireties.

GOVERNMENT SUPPORT

This invention was made with Government support under contract numbers AI83215 and AI099081 awarded by the National Institutes of Health. The Government has certain rights in the invention.

FIELD OF THE INVENTION

The field of the invention relates to gene expression.

INCORPORATION-BY-REFERENCE OF SEQUENCE LISTING

The contents of the text file named "29297-106N01US_Sequence_Listing.txt", which was created on Nov. 3, 2015, and is 57 KB in size, are hereby incorporated by reference in their entireties.

BACKGROUND OF THE INVENTION

Viruses have been used to transduce genes of interest into mammalian cells for laboratory research and for clinical purposes. This approach has allowed expression and overexpression of proteins of interest as well as the understanding of both virus life cycles and eukaryotic cell mechanisms. Gene transduction used to treat genetic diseases, cancer, and more recently has been proposed as an approach to treat infectious diseases, vascular diseases and others disorders, e.g., Alzheimer's and Parkinson's disease. Viral vectors have been progressively modified in order to increase their transduction efficiency and to reduce their toxicity, immunogenicity and inflammatory potential. Limitations of gene expression systems include low or inadequate expression of the nucleic acid of interest or therapeutic gene.

SUMMARY OF THE INVENTION

The compositions and methods of the invention provide a solution to this problem by augmenting expression of nucleic acids sought to be expressed for research or clinical purposes. The methods and compositions are compatible with any existing approach for gene therapy or gene transfection, e.g., using viral or plasmid vectors, in vivo, in vitro or ex vivo. Accordingly, a method for augmenting expression of a heterologous nucleic acid in a eukaryotic cell or increasing the efficiency of gene expression using any gene expression system includes a step of decreasing expression or activity of an endogenous Interferon-induced protein-16 (IFI16). For example, the cell is contacted with an inhibitor of IFI16 expression or activity, i.e., the inhibitor is delivered to the cell, and inhibition of IFI16 leads to increasing the amount of gene expression, e.g., encoded by a heterologous nucleic acid sequence compared to the level or amount of gene expression in the absence of the inhibitor. For example, the increase is at least 10%, 25%, 50%, 2-fold, 5-fold, 10-fold or more.

Heterologous nucleic acid means that the nucleic acid has a sequence that does not naturally occur in the cell into which the nucleic acid is introduced. For example, the nucleic acid may encode a same or different protein of a different species from the cell into which the nucleic acid is introduced. Alternatively, the heterologous nucleic acid encodes a different form, isotype, or version of a protein compared to that which is present in the cell into which the nucleic acid is introduced. For example, the host or recipient cell contains a defective or mutated nucleic acid (encoding a functionally defective, non-functional, or otherwise compromised gene product) and the heterologous nucleic acid has a different sequence that encodes a normal, correct, and functionally active gene product/protein. Heterologous expression means production of a gene product that a cell that does not normally make (i.e., express). Heterologous (meaning 'derived from a different organism') refers to the fact that often the transferred protein was initially cloned from or derived from a different cell type or a different species from the recipient. Genetic material coding for the protein, e.g., complementary DNA (cDNA) is added to the recipient cell and expressed under the control of promoter sequences that are operably linked to the DNA in an expression vector. For example, the vector is a plasmid or a viral vector, e.g., Herpes virus vector, retroviral vector (e.g., lentiviral vector), adenoviral vector, adeno-associated viral vector. Methods for transferring foreign genetic material into a recipient cell include transfection and transduction.

The heterologous nucleic acid encodes a transgene or gene/gene product sought to be expressed to clinical benefit or for research purposes. For example, the gene sought to be expressed is encoded by non-viral DNA cloned into a plasmid or viral vector. Typically, the gene or heterologous nucleic acid sought to be expressed is a mammalian nucleic acid, e.g. purified cDNA, in a plasmid or viral vector. Heterologous nucleic acids comprise a coding sequence. For example, the heterologous nucleic acid coding sequence comprises non-viral DNA or encodes a mammalian gene product. Preferably, the heterologous nucleic acid comprises vectored DNA. For example, the vector comprises a coding sequence of a gene product that is non-viral. In another example, the coding sequence encodes a viral gene product, e.g., a gene product to which an antiviral immune response is elicited for prophylactic or therapeutic purposes.

The cell is a human cell or another mammalian non-human cell such as a dog or cat, i.e., the methods and compositions are applicable to human gene therapy as well as veterinary uses for companion animals, performance animals, e.g., horses, or livestock.

The IFI16 gene comprises the nucleic acid sequence and amino acid sequences provided in GENBANK Accession numbers NM_005531.2 or M63838.1. The sequences for the mouse homologue of IFI16 is provided in GENBANK Accession number NM_008329.2. Expression is decreased by contacting the cell or tissue with an siIFI16-specific siRNA. For example, siRNA sequences include 5'GAUCUGUAAUUCAUAGUCA3'(SEQ ID NO 6), 5'GGACCAGCCCUAUCAAGAA3'(SEQ ID NO 7), 5'GGAGUAAGGUGUCCGAGGA3'(SEQ ID NO 8), 5'CAGCGUAACUCCUAAAAUC3'(SEQ ID NO 9), and 5'GCUGGUCCUAACCAAACGU3'(SEQ ID NO 10), or for longer term effects, the expression is decreased by contacting the cell with an IFI16-specific shRNA. Exemplary IFI16 shRNAs include the following shRNA sequences that knockdown IFI16 expression:

```
#1
Sense:
                                       (SEQ ID NO 11)
CCACAAUCUACGAAAUUCA Anti-sense:
                                       (SEQ ID NO 12)
UGAAUUUCGUAGAUUGUGG

#2
Sense:
                                       (SEQ ID NO 13)
CCAUCCAGCAGUUUCUUCA Anti-sense:
                                       (SEQ ID NO 14)
UGAAGAAACUGCUGGAUGG

#3
Sense:
                                       (SEQ ID NO 15)
GGAAGGAGAUAAACUGAAA Anti-sense:
                                       (SEQ ID NO 16)
UUUCAGUUUAUCUCCUUCC.
```

The shRNA is provided in a vector for administration to the cell to be treated. In yet another example, IFI16 expression is decreased by contacting the cell with an IFI16-specific antisense nucleic acid. For example, the antisense sequence is complementary to some or all of the gene sequence of IFI16.

In another approach, IFI16 activity is modulated. For example, the activity is decreased by contacting the cell with an inhibitor of IFI16 binding to DNA. For example, the inhibitor is a small molecule, i.e., a compound with a molecular mass of less than 1000 daltons. Small molecules are also used to increase IFI16 activity.

Also within the invention is an expression vector that contains an heterologous coding sequence, e.g., a nucleic acid encoding a gene product sought to be expressed, and an IFI16 regulating nucleic acid sequence. The IFI16 regulating nucleic acid sequences is one that decreases expression of an endogenous IFI16 gene. For example, the IFI16-regulating nucleic acid sequence comprises an IFI16-specific shRNA, e.g., in the context of a vector, or an IFI-16-specific siRNA.

A method of modulating homologous recombination of a heterologous DNA or lentiviral vector integration in a eukaryotic cell is carried out by contacting a target cell with an inhibitor of IFI16 expression or activity. The inhibitor reduces binding of IFI16 to unchromatinized heterologous DNA or reduces IFI16-mediated addition of silencing chromatin to said heterologous DNA. IFI16 inhibition leads to increased copy number of desired gene coding sequences and/or an increase in the number of cells expressing the desired coding sequence or transgene. IFI16 inhibit leads to more integration events compared to cells that were not contacted with IFI16 inhibitory agents.

In an alternative embodiment, a method of modulating homologous recombination of a heterologous DNA or lentiviral vector integration in a eukaryotic cell comprising contacting the cell with a compound that increases IFI16 expression or activity. IFI16 is increased using small molecules. IFI16 expression is increased by treatment with interferon, e.g., contacting cells with interferon ex vivo.

Screening methods are also included. A method of identifying a IFI16-inhibitory compound is carried out by providing a eukaryotic cell infected with a Herpes virus comprising a heterologous nucleic acid encoding a detectable marker such as a fluorescent compound. The cell is contacted with a candidate compound expression of the detectable marker is measured. A decrease in expression of the detectable marker indicates that the candidate compound comprises IFI16-inhibitory activity.

A typical detectable marker comprises a green fluorescent protein (GFP). However, other detectable markers are well known in the art and suitable for the assay. The heterologous nucleic acid comprises any foreign nucleic acid relative to the host cell into which the nucleic acid is introduced. For example, the nucleic acid is a DNA molecule encoding a gene product that is not encoded by DNA in the host cell. In another example, the nucleic acid is a duplicate copy of a DNA molecule of a gene product that is naturally expressed by the host cell. In the latter situation, the objective of the gene therapy is to increase expression of a copy of an endogenous gene that is normally expressed by the cell. In another example, the nucleic acid to be expressed is an altered sequence relative to an endogenous sequence, e.g., to replace a faulty gene with a correct or normal sequence, thereby yielding a functional gene product or gene product with improved function relative to an endogenous sequence. For example, cystic fibrosis (CF) is caused by a mutation in the gene for the protein cystic fibrosis transmembrane conductance regulator (CFTR) and gene therapy is used to replace the faulty gene with the one that encodes a properly functional gene product. In another example, gene replacement therapy replaces chemokine receptors that act as co-receptors for HIV. In this example replacement gene products (CCR5 and CXCR4 receptors) shield the cells from HIV entry via both the CCR5 and CXCR4 receptors. In yet another example, hemophilia B is treated by delivery to a patient a viral vector carrying a good version of the human gene for the clotting agent known as Factor IX, which is defective in hemophilia patients. Another example, RPE65 gene replacement improved visual function in humans who suffer from Leber congenital amaurosis (LCA) Leber congenital amaurosis (LCA) caused by mutations in the gene RPE65. As was described above, expression of these and other vectored heterologous nucleic acids are improved by co-administration of IFI16 inhibitors, e.g., encoded by the same vector as the heterologous nucleic acid, or administered separately.

A compound (e.g., small molecule) or macromolecule (e.g., nucleic acid, polypeptide, or protein) of the invention is purified and/or isolated. Polynucleotides, polypeptides, or other compounds used in the invention are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state.

Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

An "isolated nucleic acid" is a nucleic acid, the structure of which is not identical to that of any naturally occurring nucleic acid, or to that of any fragment of a naturally occurring genomic nucleic acid spanning more than three separate genes. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

Antibodies and fragments thereof described herein include, but are not limited to, polyclonal, monoclonal, chimeric, dAb (domain antibody), single chain, Fab, Fab' and F(ab')2 fragments, Fv, scFvs. A fragment of an antibody possess the immunological activity of its respective antibody. In some embodiments, a fragment of an antibody contains 1500 or less, 1250 of less, 1000 or less, 900 or less, 800 or less, 700 or less, 600 or less, 500 or less, 400 or less, 300 or less, 200 or less amino acids. For example, a protein or peptide inhibitor contains 1500 or less, 1250 of less, 1000 or less, 900 or less, 800 or less, 700 or less, 600 or less, 500 or less, 400 or less, 300 or less, 200 or less, 100 or less, 80 or less, 70 or less, 60 or less, 50 or less, 40 or less, 30 or less, 25 or less, 20 or less, 10 or less amino acids. For example, a nucleic acid inhibitor of the invention contains 400 or less, 300 or less, 200 or less, 150 or less, 100 or less, 90 or less, 80 or less, 70 or less, 60 or less, 50 or less, 40 or less, 35 or less, 30 or less, 28 or less, 26 or less, 24 or less, 22 or less, 20 or less, 18 or less, 16 or less, 14 or less, 12 or less, 10 or less nucleotides. Intrabody inhibitors are also encompassed by the invention.

By "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

Other inhibitors include a nucleic acid inhibitor is a short interfering RNA, a short hairpin RNA, antisense RNA, aptamers, peptide nucleic acids (PNAs), microRNAs (miRNAs), or locked nucleic acids (LNAs). In some embodiments, the nucleic acid comprises modified oligonucleotides (e.g., 2'-o-methyl RNA).

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

DETAILED DESCRIPTION

Figure 1A:
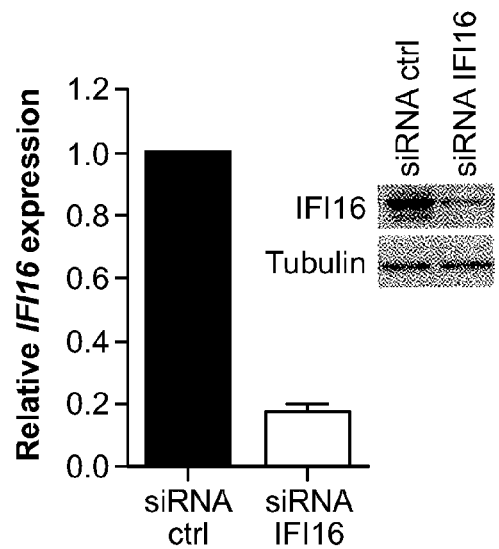
FIGS. 1A-D are bar graphs showing that IFI16 negatively regulates the replication of an ICP0-null virus. (A) IFI16 and (B) STING transcript and protein levels were decreased following transfection of HFF with either nontarget control, IFI16-specific, or STING-specific siRNAs. (C) IFI16 knockdown resulted in an increase in ICP0-null virus replication relative to cells transfected with control siRNAs. siRNA-transfected cells were infected with HSV-1 ICP0-null (7134) or a rescue virus (7134R) at an multiplicity of infection (MOI) of 0.1, harvested at 48 hpi, and virus yield was determined by plaque assay on U2OS cells. (D) IFI16 or STING knockdown decreased IFNβ transcript levels in response to ICP0-null virus infection. siRNA-transfected cells were infected with HSV-1 ICP0-null virus at an MOI of 10, and RNA was harvested at 6 hpi. Results are an average of three-(A and B), four-(C) or two-(D) independent experiments, and error bars represent the standard error of means.

The cellular DNA sensor, interferon-induced protein 16 or IFI16, was found to have a restrictive effect on herpes simplex virus gene expression and replication. This intrinsic resistance activity is independent of its role in inducing type I interferons through IRF-3 signaling. IFI16 also reduces expression of genes on transfected plasmids. The IFI16-mediated restriction is due to epigenetic silencing of the foreign DNA molecules. Therefore, IFI16 is an element of a broad restriction mechanism of foreign DNA entering the cell nucleus and lacking chromatin.

The discovery was exploited to develop a method of altering gene expression of foreign DNA introduced into eukaryotic cells. IFI16 reduces viral and transfected gene expression. Therefore, a means to reduce IFI16 expression and/or function leads to an increase in gene expression from foreign DNA in cells whether delivered from a viral vector or transfected plasmid DNA. Such methods are useful in gene delivery protocols either in cell culture, ex vivo gene therapy, or in vivo.

IFI16 also affects integration of retroviral vectors. Therefore, altering IFI16 expression and/or function increases integration of lentiviral vectors in cells in cell culture, ex vivo gene therapy, or in vivo. For example, decreasing IFI16 is increases the amount of transgene integrated and/or the number of cells into which the transgene is integrated, thereby increasing the amount of desired gene product made.

IFI16 affect recombination or gene conversion events as well. Thus, modulation of IFI16 expression and/or function increases gene conversion in gene therapy approaches in cells in culture, in vivo gene therapy, or in vivo. For example, IFI16 expression or activity is inhibited.

HSV-1 recombinant strains are useful in a screen for up- and down-regulatory compounds for regulation of IFI16 activity.

Intrinsic Immune Response Mechanisms

Classically, the host mechanisms blocking viral infection have been divided into two distinct arms of host immunity: the innate and adaptive immune responses. A third aspect of host immunity is termed intrinsic resistance. A major difference between these three responses is the constitutive expression of resistance mechanisms. A lag phase associated with the expansion of effector T and B cells characterizes adaptive immunity, making this arm the slowest of the host response. Both innate and intrinsic immunity act at the primary site of infection and mediate an initial cell-based immune response. However, while innate immunity requires de novo cellular gene expression to mediate its antiviral effects (e.g., induction of type I interferons), intrinsic resistance acts immediately to counteract viral infection through constitutively expressed proteins, known as intrinsic resistance factors. These two cell-based responses are closely linked. Many resistance factors are upregulated by type I interferons induced by the innate immune response.

The first intrinsic resistance factors to be characterized were identified as mediators of antiretroviral resistance. For instance, TRIM5α inhibits retroviral infection by modulating the capsid uncoating process (1), while APOBEC3G is incorporated into newly synthesized retrovirus capsids and induces the hypermutation of reverse transcribing RNA (2). In addition, tetherin/Bst-2 inhibits viral release by tethering viral particles to the cell surface (3). The mechanisms employed by these retroviral restriction factors are closely linked to the lifecycle of the viruses they target, and as such are thought to have developed during a long-term co-evolution of these viruses with their respective hosts. Members of the Herpesviridae family, including herpes simplex viruses (HSV), have also co-evolved with their hosts, indicated by their high seroprevalence but modest pathogenicity. Prior to the invention, little was known about intrinsic resistance factors that target these large DNA viruses.

The most well characterized intrinsic immune response to herpesvirus infection involves the action of promyelocytic leukemia protein nuclear bodies (PML NB), also known as nuclear domain 10 (ND10) bodies. These dynamic sub-nuclear domains are made up of a variety of cellular proteins, and have been implicated in several cellular responses, including gene expression, DNA damage, apoptosis, and aging. During HSV-1 infection, ND10 components accumulate de novo in the nucleus at sites near incoming viral DNA, and this is associated with their ability to restrict viral gene expression. HSV-1 overcomes this restriction through expression of the viral ICP0 immediate-early protein, an E3 ubiquitin ligase that disrupts ND10 by promoting degradation of the associated PML and Sp100 proteins. The importance of counteracting this intrinsic response is documented by reports that ICP0-null viruses are significantly attenuated for viral replication, particularly in primary human fibroblasts. However, depletion of ND10 by simultaneous knockdown of the three major ND10 components, PML, Sp100 and hDAXX does not completely rescue the replication of an ICP0-null virus, indicating additional mechanisms are involved in the intrinsic resistance to HSV-1.

IFI16 DNA sensor restricts human cytomegalovirus (HCMV) replication in human fibroblasts. While IFI16 is known to promote IRF-3 signaling in response to herpesvirus infection, the reported IFI16-dependent restriction of HCMV was independent of IFNβ, indicating IFI16 may act as an intrinsic resistance factor in addition to categorization as an innate pattern recognition receptor. IFI16 was identified as a target of ICP0-mediated degradation. Thus, studies were undertaken to evaluate IFI16's activity as an intrinsic resistance factor to HSV infection. IFI16 was found to restrict HSV-1 replication in the absence of ICP0 and this phenotype is independent of STING and ND10-mediated intrinsic resistance. In addition, overexpression of a functional IFI16 in permissive U2OS cells confers resistance to an ICP0-null virus. Furthermore, IFI16 acts by silencing the expression of both viral and transfected DNA.

IFI16 Acts as an Intrinsic Resistance Factor to Silence HSV-1 and Transfected DNA Gene Expression The intrinsic cell resistance to infection by large DNA viruses involves the silencing of viral DNA in the nucleus. During herpes simplex virus 1 (HSV-1) infection the ICP0 immediate-early protein counteracts this cellular response in part by disrupting ND10 bodies. However, ND10 components do not account for the total restriction observed in the absence of ICP0, indicating that additional unidentified mechanisms contribute to silencing the viral genome.

As described below, nuclear IFI16 DNA sensor was found to act as an intrinsic factor involved in repression of foreign DNA. Knockdown of IFI16 enhanced the replication and immediate-early gene expression of an ICP0-null virus. This phenotype was independent of downstream STING signaling, and knockdown of IFI16 did not affect ND10 accumulation at viral genomes. Furthermore, overexpression of exogenous IFI16 in the permissive U2OS cell line restricted ICP0-null virus gene expression. The repressive activity of IFI16 was not limited to viral DNA as the expression of transfected DNA was also inhibited by IFI16. These results indicate that in addition to its involvement as an innate pattern recognition receptor, IFI16 mediates an intrinsic immune response to foreign DNA by silencing its expression. This activity can be exploited to improve expression of any heterologous gene or nucleic acid sequence sought to be expressed in a eukaryotic cell for therapeutic purposes, e.g., in vivo or ex vivo gene therapy, industrial purposes, e.g., large scale production and purification of proteins, or for research purposes, e.g., overexpression of proteins to study function. With IFI16 inhibition, expression of the heterologous nucleic acid (transgene) is increased at least 10%, 20%, 50%, 2-fold, 3-fold, and up to 10-fold or more. For example, gene expression is generally in the range of 3-5 fold higher with IFI16 inhibition, e.g., siRNA or ShRNA, compared to the amount in the absence of IFI16 inhibition.

DNA Binding Domains of IFI16

DNA binding domains of IFI 116 represent regions that are targeted by small molecule inhibitors, antibodies or fragments thereof, as well as antibodies that are expressed intracellularly, i.e., intrabodies. Certain amino acids are important for DNA binding.

Location of HIN domains (DNA binding domains): amino acids 201 to 370 and amino acids 518 to 684. K663, R667, K732, K734, and R764 make connections with DNA backbone (amino acids underlined below, see also FIG. 10) (Jin et al., 2012 Immunity 36, 561-571; hereby incorporated by reference). Mutations K732A, K734A, and K759A disrupt DNA binding ability. Small molecules or other inhibitors such as peptide or antibodies (or antibody fragments) that contact IFI16 in one or both HIN domains or at or in the vicinity of residues K663, R667, K732, K734, K759, and/or R764 reduce or inhibit IFI16 binding to DNA, thereby decreasing or inhibiting IFI16 activity or conformational change. The amino acid coordinates are relative to the A isoform of ISI16; however, those same regions and corresponding amino acid coordinates relative to B and C isoforms have the same function. An intrabody is an antibody that has been designed to be expressed intracellularly and can be directed to a specific target antigen present in various subcellular locations including the cytosol, nucleus, endoplasmic reticulum (ER), mitochondria, peroxisomes, plasma membrane and trans-Golgi network (TGN) through in frame fusion with intracellular trafficking/localization peptide sequences. (Lo et al., 2008, Handb Exp Pharmacol. 181: 343-73; Ali K, Southwell A L, Bugg C W, et al. Recombinant Intrabodies as Molecular Tools and Potential Therapeutics for Huntington's Disease. In: Lo D C, Hughes R E, editors. Neurobiology of Huntington's Disease: Applications to Drug Discovery, pp. 255-66, Boca Raton, Fla.: CRC Press; 2011; both of which are hereby incorporated by reference.)

The following materials and methods were used to generate the data described herein.

IFI16 Sequences:

Human interferon-gamma induced protein (IFI 16) gene, complete cds is available at GenBank Accession No. M63838.1, hereby incorporated by reference.

```
Location/Qualifiers
source      1..2709
                /organism="Homo sapiens"
                /mol_type="mRNA"
                /db_xref="taxon:9606"
                /cell_line="CTL/NK cell"
gene        1..2709
                /gene="IFI 16"
5'UTR       1..264
                /gene="IFI 16"
CDS         265..2454
                /gene="IFI 16"
                /codon_start=1
                /product="interferon-gamma induced protein"
                /protein_id="AAA58683.1"
                /db_xref="GI:184569"
                /translation="
```

Amino acid sequence: (SEQ ID NO: 1)

MGKKYKNIVLLKGLEVINDYHFRMVKSLLSNDLKLNLKMREEYD

KIQIADLMEEKERGDAGLGKLIKIFEDIPTLEDLAETLKKEKLK

VKGPALSRKRKKEVHATSPAPSTSSTVKTEGAEATPGAQKRKKS

TKEKAGPKGSKVSEEQTQPPSPAGAGMSTAMGRSPSPKTSLSAP

PNSSSTENPKTVAKCQVTPRRNVLQKRPVIVKVLSTTKPFEYET

PEMEKKIMEHATVATQTQFFHVKVLNTSLKEKENGKKIIIISDY

LEYDSLLEVNEESTVSEAGPNQTFEVPNKIINRAKETLKIDILH

KQASGNIVYGVFMLHKKTVNQKTTIYEIQDDRGKMDVVGTGQCH

NIPCEEGDKLQLFCERLRKKNQMSKLISEMHSFIQIKKKTNPRN

NDPKSMKLPQEQRQLPYPSEASTTEPESHLRTPQMPPTTPSSSF

ETKKSEDTISKMNDFMRMQILKEGSHFPGPFMTSIGPAESHPHT

PQMPPSTPSSSFLTTLKPRLKTEPEEVSIEDSAQSDLKEVMVLN

ATESFVYEPKEQKKMFHATVATENEVFRVKVFNIDLKEKFTPKK

HAIANYVCRNGFLEVYPFTLVADVNADRNMEIPKGLIRSASVTP

KINQLCSQTKGSFVNGVELVHKKNVRGEFTYYEIQDNTGKMEVV

VHGRLNTINCEEGDKLKLTSFELAPKSGNTGELRSVIHSHIKVI

KTRKNKKDILNPDSSMETSPDFFF

```
polyA_signal 2677..2686
    /gen="IFI 16"
```

-continued

Nucleotide sequence:
(SEQ ID NO: 5)

```
   1  gggaatagca gaataggagc aagccagcac tagtcagcta actaagtgac tcaaccaagg
  61  cctttttcc ttgttatctt tgcagatact tcattttctt agcgtttctg gagattacaa
 121  catcctgcgg ttccgtttct gggaacttta ctgatttatc tccccctca cacaaataag
 181  cattgattcc tgcatttctg aagatctcaa gatctggact actgttgaaa aaatttccag
 241  tgaggctcac ttatgtctgt aaagatggga aaaaaataca agaacattgt tctactaaaa
 301  ggattagagg tcatcaatga ttatcatttt agaatggtta agtccttact gagcaacgat
 361  ttaaaactta atttaaaaat gagagaagag tatgacaaaa ttcagattgc tgacttgatg
 421  gaagaaaagt tccgaggtga tgctggtttg ggcaaactaa taaaaatttt cgaagatata
 481  ccaacgcttg aagacctggc tgaaactctt aaaaaagaaa agttaaaagt aaaaggacca
 541  gccctatcaa gaaagaggaa gaaggaagtg catgctactt cacctgcacc ctccacaagc
 601  agcactgtca aaactgaagg agcagaggca actcctggag ctcagaaaag aaaaaaatca
 661  accaaagaaa aggctggacc caaagggagt aaggtgtccg aggaacagac tcagcctccc
 721  tctcctgcag gagccggcat gtccacagcc atgggccgtt ccccatctcc caagacctca
 781  ttgtcagctc cacccaacag ttcttcaact gagaacccga aaacagtggc caaatgtcag
 841  gtaactccca gaagaaatgt tctccaaaaa cgcccagtga tagtgaaggt actgagtaca
 901  acaaagccat ttgaatatga accccagaa atggagaaaa aataatgtt tcatgctaca
 961  gtggctacac agacacagtt cttccatgtg aaggttttaa acaccagctt gaaggagaaa
1021  ttcaatggaa agaaaatcat catcatatca gattatttgg aatatgatag tctcctagag
1081  gtcaatgaag aatctactgt atctgaagct ggtcctaacc aaacgtttga ggttccaaat
1141  aaaatcatca acagagcaaa ggaaactctg aagattgata ttcttcacaa acaagcttca
1201  ggaaatattg tatatggggt atttatgcta cataagaaaa cagtaaatca gaagaccaca
1261  atctacgaaa ttcaggatga tagaggaaaa atggatgtag tggggacagg acaatgtcac
1321  aatatcccct gtgaagaagg agataagctc cagcttttct gctttcgact tagaaaaaag
1381  aaccagatgt caaaactgat ttcagaaatg catagtttta tccagataaa gaaaaaaaca
1441  aacccgagaa acaatgaccc caagagcatg aagctacccc aggaacagcg tcagcttcca
1501  tatccttcag aggccagcac aaccttccct gagagccatc ttcggactcc tcagatgcca
1561  ccaacaactc catccagcag tttcttcacc aagaaaagtg aagacacaat ctccaaaatg
1621  aatgacttca tgaggatgca gatactgaag gaagggagtc attttccagg accgttcatg
1681  accagcatag gcccagctga gagccatccc cacactcctc agatgcctcc atcaacacca
1741  agcagcagtt tcttaaccac gttgaaacca agactgaaga ctgaacctga agaagtttcc
1801  atagaagaca gtgcccagag tgacctcaaa gaagtgatgg tgctgaacgc aacagaatca
1861  tttgtatatg agcccaaaga gcagaagaaa atgtttcatg ccacagtggc aactgagaat
1921  gaagtcttcc gagtgaaggt tttaatatt gacctaaagg agaagttcac cccaaagaag
1981  atcattgcca tagcaaatta tgtttgccgc aatgggttcc tggaggtata tcctttcaca
2041  cttgtggctg atgtgaatgc tgaccgaaac atggagatcc aaaaggatt gattagaagt
2101  gccagcgtaa ctcctaaaat caatcagctt tgctcacaaa ctaaaggaag ttttgtgaat
2161  ggggtgtttg aggtacataa gaaaaatgta aggggtgaat tcacttatta tgaaatacaa
2221  gataatacag ggaagatgga agtggtggtg catggacgac tgaacacaat caactgtgag
2281  gaaggagata aactgaaact caccagcttt gaattggcac cgaaaagtgg gaataccggg
2341  gagttgagat ctgtaattca tagtcacatc aaggtcatca agaccaggaa aaacaagaaa
```

```
2401  gacatactca atcctgattc aagtatggaa acttcaccag acttttcct ctaaaatctg 2461  gatgtcattg acgataatgt ttatggagat aaggtctaag tccctaaaaa aatgtacata 2521  tacctggttg aaatacaaca ctatacatac acaccaccat atatactagc tgttaatcct 2581  atggaatggg ggtattggga gtgcttttt aattttcat agtttttttt taataaaatg 2641  gcatattttg catctacaac ttctataata agaaaaaata aataaacatt atctttttg 2701  tgaaaaaaa
```

Human IFI16 has three isoforms (A, B, and C). The mouse homologue of human IFI16 is termed p204. Nucleic acid and amino acid sequences for these isoforms and the homologue follow.

Isoform 1 (IFI16 A)

1...785

Protein Sequence
(SEQ ID NO: 2)

MGKKYKNIVLLKGLEVINDYHFRMVKSLLSNDLKLNLKMREEYDKIQIADLMEEK

FRGDAGLGKLIKIFEDIPTLEDLAETLKKEKLKVKGPALSRKRKKEVDATSPAPS

TSSTVKTEGAEATPGAQKRKKSTKEKAGPKGSKVSEEQTQPPSPAGAGMSTAMGR

SPSPKTSLSAPPNSSSTENPKTVAKCQVTPRRNVLQKRPVIVKVLSTTKPFEYET

PEMEKKIMFHATVATQTQFFHVKVLNTSLKEKENGKKIIIISDYLEYDSLLEVNE

ESTVSEAGPNQTFEVPNKIINRAKETLKIDILHKQASGNIVYGVFMLHKKTVNQK

TTIYEIQDDRGKMDVVGTGQCHNIPCEEGDKLQLFCFRLRKKNQMSKLISEMHSF

IQIKKKTNPRNNDPKSMKLPQEQRQLPYPSEASTTFPESHLRTPQMPPTTPSSSF

FTKKSEDTISKMNDFMRMQILKEGSHFPGPFMTSIGPAESHPHTPQMPPSTPSSS

FLTTKSEDTISKMNDFMRMQILKEGSHFPGPFMTSIGPAESHPHTPQMPPSTPSS

SFLTTLKPRLKTEPEEVSIEDSAQSDLKEVMVLNATESFVYEPKEQKKMFHATVA

TENEVERVKVFNIDLKEKFTPKKIIAIANYVCRNGFLEVYPFTLVADVNADRNME

IPKGLIRSASVTPKINQLCSQTKGSFVNGVFEVHKKNVRGEFTYYEIQDNTGKME

VVVHGRLTTINCEEGDKLKLTCFELAPKSGNTGELRSVIHSHIKVIKTRKNKKDI

LNPDSSMETSPDFFF

Isoform 2 (IFI16 B)

Amino acids 444-499 from Isoform 1 are missing

VERSION NP_005522.2 GI:112789562
DB SOURCE REFSEQ: accession NM 005531.2 (hereby incorporated by reference)

Location/Qualifiers
source      1..729

/organism="Homo sapiens"

/db_xref="taxon:9606"

/chromosome="1"

/map="1q22"

-continued

Protein Sequence (SEQ ID NO: 3)

MGKKYKNIVLLKGLEVINDYHFRMVKSLLSNDLKLNLKMREEYDKIQIADLME
EKFRGDAGLGKLIKIFEDIPTLEDLAETLKKEKLKVKGPALSRKRKKEVDATS
PAPSTSSTVKTEGAEATPGAQKRKKSTKEKAGPKGSKVSEEQTQPPSPAGAGM
STAMGRSPSPKTSLSAPPNSSSTENPKTVAKCQVTPRRNVLQKRPVIVKVLST
TKPFEYETPEMEKKIMFHATVATQTQFFHVKVLNTSLKEKFNGKKIIIISDYL
EYDSLLEVNEESTVSEAGPNQTFEVPNKIINRAKETLKIDILHKQASGNIVYG
VFMLHKKTVNQKTTIYEIQDDRGKMDVVGTGQCHNIPCEEGDKLQLFCFRLRK
KNQMSKLISEMHSFIQIKKKTNPRNNDPKSMKLPQEQRQLPYPSEASTTFPES
HLRTPQMPPTTPSSSFFTKKSEDTISKMNDFMRMQILKEGSHFPGPFMTSIGP
AESHPHTPQMPPSTPSSSFLTTLKPRLKTEPEEVSIEDSAQSDLKEVMVLNAT
ESFVYEPKEQKKMFHATVATENEVFRVKVFNIDLKEKFTPKKIIAIANYVCRN
GFLEVYPFTLVADVNADRNMEIPKGLIRSASVTPKINQLCSQTKGSFVNGVFE
VHKKNVRGEFTYYEIQDNTGKMEVVVHGRLTTINCEEGDKLKLTCFELAPKSG
NTGELRSVIHSHIKVIKTRKNKKDILNPDSS
METSPDFFF

Isoform 3 (IFI16 C)

1...673

Amino acids 444-555 from Isoform 1 are missing

Protein Sequence (SEQ ID NO: 4)

MGKKYKNIVLLKGLEVINDYHFRMVKSLLSNDLKLNLKMREEYDKIQIADLME
EKFRGDAGLGKLIKIFEDIPTLEDLAETLKKEKLKVKGPALSRKRKKEVDATS
PAPSTSSTVKTEGAEATPGAQKRKKSTKEKAGPKGSKVSEEQTQPPSPAGAGM
STAMGRSPSPKTSLSAPPNSSSTENPKTVAKCQVTPRRNVLQKRPVIVKVLST
TKPFEYETPEMEKKIMEHATVATQTQFFHVKVLNTSLKEKENGKKIIIISDYL
EYDSLLEVNEESTVSEAGPNQTFEVPNKIINRAKETLKIDILHKQASGNIVYG
VFMLHKKTVNQKTTIYEIQDDRGKMDVVGTGQCHNIPCEEGDKLQLFCFRLRK
KNQMSKLISEMHSFIQIKKKTNPRNNDPKSMKLPQEQRQLPYPSEASTTFPES
HLRTPQMPPTTPSSSFFTKLKPRLKTEPEEVSIEDSAQSDLKEVMVLNATESF
VYEPKEQKKMFHATVATENEVERVKVFNIDLKEKFTPKKHAIANYVCRNGFLE
VYPFTLVADVNADRNMEIPKGLIRSASVTPKINQLCSQTKGSFVNGVFEVHKK
NVRGEFTYYEIQDNTGKMEVVVHGRLTTINCEEGDKLKLTCFELAPKSGNTGE
LRSVIHSHIKVIKTRKNKKDILNPDSSMETSPDFFF p204 sequence NM_008329.2 (hereby incorporated by reference)
Location/Qualifiers
source      1..2302
            /organism="Mus musculus"
            /mol_type="mRNA"
            /strain="C57BL/6"
            /db_xref="taxon:10090"
            /gene="Ifi204"

-continued

/gene_synonym="Ifi16; p204"

/note="interferon, gamma-inducible protein 16; interferon, gamma-inducible gene 204; ifi-204; interferon-inducible protein p204"

/codon_start=1

/product="interferon-activable protein 204"

/protein_id="NP 032355.2"

/dbxref="GI:118130979"

/db_xref="CCDS:CCDS35792.1"

/db_xref="GeneID:15951"

/db_xref="MGI:96429"

(SEQ ID NO 17)
/translation="MVNEYKRIVLLRGLECINKHYFSLEKSLLARDLNLERDNQEQ
YTTIQIANMMEEKEPADSGLGKLIAFCEEVPALRKRAEILKKERSEVTGETSLEKN
GQEAGPATPTSTTSHMLASERGETSATQEETSTAQAGTSTAQARTSTAQAGTSTAQ
KRKIMREEETGVKKSKAAKEPDQPPCCEEPTARCQSPILHSSSSASSNIPSAKNQK
SQPQNQNIPRGAVLHSEPLTVMVLTATDPFEYESPEHEVKNMLHATVATVSQYFHV
KVFNINLKEKFTKKNFIIISNYFESKGILEINETSSVLEAAPDQMIEVPNSIIRNA
NASPKICDIQKGTSGAVFYGVFTLHKKTVNRKNTIYEIKDGSGSIEVVGSGKWHNI
NCKEGDKLHLFCFHLKTIDRQPKLYCGEHSFIKISKRGNYPKEPAKEEDHHHGPKQ
YMYLKYTEPFTYDLKEDKRMFHATVATETEFFRVKVFDTALKSKFIPRNIIAISDY
FGCNGFLEIYRASCVSDVNVNPTMVISNTLRQRANATPKISYLFSQARGTEVSGEY
LVNKKTERNKFIYYGIGDDTGKMEVVVYGRLTNVRCEPGSKLRLVCFELTSTEDGW
QLRSVRHSYMQVINARK"

Nucleotide Sequence:
(SEQ ID NO 18)
```
  1  agtttcttat ttactgactt agctgcctac ctactcaagc caagcaggcc acttcttgac
 61  ccggtgaagg tctcaggatc tgtacatcac tgcagaaata tccaggaagg ctcagcaaca
121  acttcaaaga tggtgaatga atacaagaga attgttctgc tgagaggact tgaatgtatc
181  aataagcatt attttagctt atttaagtca ttgctggcca gagatttaaa tctggaaaga
241  gacaaccaag agcaatacac cacgattcag attgctaaca tgatggaaga gaaatttcca
301  gctgattctg gattgggcaa actgattgcg ttttgtgaag aagtaccagc tcttagaaaa
361  cgagctgaaa ttcttaaaaa agagagatca gaagtaacag agaaacatc actggaaaaa
421  aatggtcaag aagcaggtcc tgcaacacct acatcaacta caagccacat gttagcatct
481  gaaagaggcg agacttctgc aacccaggaa gagacttcca cagctcaggc ggggacttcc
541  acagctcagg cgaggacttc cacagctcag gcggggactt ctacagccca gaaaagaaaa
601  attatgagag aagaagagac tggagtgaaa aagagcaagg cggctaagga accagatcag
661  cctccctgtt gtgaagaacc cacagccagg tgccagtcac aatactccca cagctcatct
721  tcagcttcat ctaacattcc ttcggctaag aaccaaaaat cacaacccca gaatcagaac
781  attcccgag gtgctgttct ccactcagag ccctgacag tgatggtgct cactgcaaca
841  gacccatttg aatatgaatc accagaacat gaagtaaaga acatgcttca tgctacagtg
901  gctacagtga gccagtattt ccatgtgaaa gttttcaaca tcaacttgaa agaaaagttc
```

```
 961   acaaaaaaga attttatcat catatccaat tactttgaga gcaaaggcat cctggagatc 1021   aatgagactt cctctgtgtt agaggctgct cctgaccaaa tgattgaagt gcccaacagt 1081   attatcagaa atgcaaatgc cagccctaag atctgtgata ttcaaaaggg tacttctgga 1141   gcagtgttct atggagtgtt tacattacac aagaaaacag tgaaccgaaa gaacacaatc 1201   tatgaaataa aagatggttc aggaagcata gaagtggtgg ggagtggaaa atggcacaac 1261   atcaactgca aggaaggaga taaactccac ctcttctgct ttcacctgaa aacaattgac 1321   aggcaaccaa agttagtgtg tggagaacac agtttcatca agatatcaaa gagaggaaat 1381   gtaccaaagg agcctgctaa ggaagaagat caccatcatg gtcccaaaca agtgatggtg 1441   ctgaaagtaa cagaaccatt tacatatgac ctgaaagagg ataaaagaat gtttcatgct 1501   accgtggcta ctgaaactga gttcttcaga gtgaaggttt ttgacacggc tctaaagagc 1561   aagttcatcc caagaaatat cattgccata tcagattatt ttgggtgcaa tgggtttctg 1621   gagatataca gagcttcctg tgtctctgat gtgaacgtta atccaacaat ggttatctca 1681   aatacactga gacaaagagc taatgcaact cctaaaattt cttatctttt ctcacaagca 1741   aggggacat ttgtgagtgg agagtactta gtaaataaga aaacggagag gaataaattc 1801   atttactatg gaattggaga tgatacaggg aaaatggaag tggtggttta tggaagactc 1861   accaatgtca ggtgtgaacc aggcagtaaa ctaagacttg tctgctttga attgacttcc 1921   actgaagatg ggtggcagct gaggtctgta aggcacagtt acatgcaggt catcaatgct 1981   agaaagtgaa ggaaagccac tcaacccaga ctcagtcggg agaacctctc tggaaccata 2041   cttctgaaaa cctgaatgcc aatgatattt ttttgtggag ataagattca attacagaaa 2101   ataaatgtgt ataagcctat tgaaatatca gtcctataaa gaccatctct taattctagg 2161   aaatggtgtt ttcttatatt ctttacacat tttctatatc taaattcatt tgttgtctct 2221   ataacttcta taactgttca atttgcaatt tttatgccta aaacttataa aaataaattc 2281   acacaatttc tgtaaaaaaa aa
//
```

Cell Culture and Viruses

Human foreskin fibroblasts (HFF) and U2OS cells were obtained from American Type Culture Collection (ATCC). HFF were grown in DMEM supplemented with 15% heat-inactivated fetal bovine serum (FBS), 2 mM L-glutamine, streptomycin, and penicillin (15% DMEM). U2OS cells were grown in DMEM supplemented with 5% heat-inactivated FBS and 5% heat-inactivated bovine calf serum (BCS). The ICP0-null (7134) and rescued 7134R viruses were grown and titred in parallel on U2OS cells using known methods, e.g., Cai et al., 1989, Journal of Virology 63(11):4579-4589.

Virus Infections

Virus was diluted in cold phosphate-buffered-saline (PBS) containing 0.1% glucose and 1% heat-inactivated BCS. Cells were infected at the stated MOI for 1 h at 37° C., washed twice with PBS and overlaid with DMEM containing 1% heat-inactivated BCS. Infected cells were incubated at 37° C. for the indicated length of time.

siRNA Transfections

Double-stranded IFI16-specific, STING-specific and non-target control siRNAs were purchased from Dharmacon (Product number L-020004-00-0005, On-Targetplus SMARTpool.)

```
ON-TARGET plus SMARTpool siRNA J-020004-08, IFI16

Target Sequence:  GAUCUGUAAUUCAUAGUCA  SEQ ID NO 19
    Mol. Wt.            Ext. Coeff
  13,384.8 (g/mol)    366,129 (L/mol-cm)

ON-TARGET plus SMARTpool siRNA J-020004-07, IFI16

Target Sequence:  GGACCAGCCCUAUCAAGAA  SEQ ID NO 20
    Mol. Wt.            Ext. Coeff
  13,444.8 (g/mol)    365,701 (L/mol-cm)

ON-TARGET plus SMARTpool siRNA J-020004-06, IFI16

Target Sequence:  GGAGUAAGGUGUCCGAGGA  SEQ ID NO 21
    Mol. Wt.            Ext. Coeff
  13,459.9 (g/mol)    364,099 (L/mol-cm)

ON-TARGET plus SMARTpool siRNA J-020004-05, IFI16

Target Sequence:  CAGCGUAACUCCUAAAAUC  SEQ ID NO 22
    Mol. Wt.            Ext. Coeff
  13,414.9 (g/mol)    375,580 (L/mol-cm)
```

Exemplary si-RNAs also include: 5'-GCUGGUC-CUAACCAAACGU-3' (IFI16 nucleotide 1106-1126. (SEQ ID NO 23)

The pooled siRNA were transfected into HFF using the DarmaFECT 2 transfection reagent (Dharmacon/Thermo Fischer Scientific; Lafayette, Colo.) at a final siRNA concentration of 5 nM according to the manufacturer's instructions. The siRNA containing media was replaced 24 hours post-transfection, and cells were assayed for IFI16 or STING levels by immunoblotting and/or infected with HSV-1 at 72 hours post-transfection (hpt).

Three examples of IFI16 shRNA sequences shRNA sequences that have been shown to knockdown IFI16 include those shown below. Others are known in the art.

```
#1
Sense:
                                     (SEQ ID NO 11)
CCACAAUCUACGAAAUUCA Anti-sense:
                                     (SEQ ID NO 12)
UGAAUUUCGUAGAUUGUGG

#2
Sense:
                                     (SEQ ID NO 13)
CCAUCCAGCAGUUUCUUCA Anti-sense:
                                     (SEQ ID NO 14)
UGAAGAAACUGCUGGAUGG

#3
Sense:
                                     (SEQ ID NO 15)
GGAAGGAGAUAAACUGAAA Anti-sense:
                                     (SEQ ID NO 16)
UUUCAGUUUAUCUCCUUCC
```

Plasmids and DNA Transfection

A N-Myc IFI16 plasmid and empty vector backbone were used for transfection experiments. U2OS cells were plated at a density to ensure 50% confluency on the day of transfection. Cells were transfected with 0.5 &g of empty vector or N-Myc IFI16 plasmid using the Effectene transfection reagent (Qiagen) and were infected with the indicated viruses at 48 hpt.

HFF were transfected with either 0.5 &g of an empty vector plasmid, pEGFP-C1 (Clonetech), or pEF1-GFP using the Lipofectamine LTX reagent (Invitrogen) at 48 hours post-siRNA treatment. Transfection media was replaced at 6 hpt with 15% DMEM and whole cell lysates were harvested and processed for FACS or western blot at 36 hpt.

Cellular RNA Analysis by qPCR

Total RNA was extracted using the Qiagen RNeasy Kit and DNase treated using the DNA-free kit (Ambion). Equal amounts of DNase-treated RNA was then reverse-transcribed and quantified by real-time PCR (qPCR) using the Power SYBR Green PCR master mix and a Prism 7300 sequence detection system (Applied Biosystems). PCR reactions were carried out in duplicate, and relative copy numbers were determined by comparison with standard curves. Mock reverse-transcribed samples were included as negative controls. Transcript levels were normalized to 18S rRNA and made relative to mock-infected samples. Experiments were conducted three times, and the values were averaged.

Western Blots

Cells were lysed in NuPAGE® LDS Sample Buffer, and proteins were resolved on NuPAGE® 4-12% Bis Tris Gels (Invitrogen). Proteins were transferred overnight to PVDF membranes and blocked with 5% milk in PBS. Membranes were probed with primary antibody at 4° C., washed with PBS containing 0.05% Tween 20 and incubated in secondary antibody for 1 h at room temperature. Western blots were developed using Luminate Forte Western HRP substrate (Millipore).

Indirect Immunofluorescence

HSV-1 infected HFF grown on coverslips were fixed with 2% formaldehyde, permeabilized with 0.5% NP40, and blocked in 5% normal goat serum. Fixed cells were incubated with antibodies for 30 min at 37° C. and washed two times with PBS containing 0.05% Tween 20 followed by one wash with PBS. Alexa Fluor 488- and 594-conjugated secondary antibodies were incubated with cells for 2 h at 25° C. The coverslips were washed as above and mounted in ProLong Gold antifade reagent (Invitrogen). Images were acquired using an Axioplan 2 microscope (Zeiss) with a 63× objective and Hamamatsu CCD camera (model C4742-95). Images were arranged in figures using Adobe Photoshop CS4 (Adobe Systems, Seattle, Wash.).

Flow Cytometry

Transfected HFF were trypsinized, pelleted and resuspended in 500 i&l Accumax cell counting solution (Millipore). Cell suspensions were passed through a 40 i&m filter to prevent clumping and stained with a 1:500 dilution of propidium iodine (PI). Fluorescence readings were collected for 20,000 cells. PI positive cells were gated out during analysis and GFP+ cells were defined on empty vector transfected cells. Data analysis was performed using FlowJo (Version 9) and graphs were constructed using GraphPad Prism software.

Antibodies

Antibodies used in Western blot experiments were mouse anti-IFI16 (ab55328, 1:1000, Abcam), mouse anti-GAPDH (G041, 1:5000, Applied Biological Materials), rabbit anti-TMEM173 (ab92650, 1:2000, Abcam), mouse anti-ICP0 (1:1000, EastCoast Bio), mouse anti-β-Tubulin (Clone JDR.3B8, 1:2000, Sigma-Aldrich), mouse anti-IFIT2 (1:1000, ABCAM), and mouse anti-Myc (9E10, 1:2000, Santa Cruz Biotechnology), HRP-conjugated goat antibodies were used at 1:5,000-1:20,000 (Santa Cruz Bio-technology).

Antibodies used for indirect immunofluorescence studies were mouse anti-IFI16 (ab55328, 1:200, Abcam), rabbit anti-ICP8 (3-83, 1:500, (17)), rabbit anti-PML (1:1000, Santa Cruz Bio-technology) and mouse anti-ICP4 (39S, 1:200, (18). Goat anti-mouse Alexa-488 (Jackson ImmunoResearch) and anti-rabbit Alexa 594 (Jackson ImmunoResearch) were used at 1:500 for secondary detection.

Primers

| Name | Use | Primer Sequence | SEQ ID NO |
|---|---|---|---|
| hIFNβ | qRT-PCR | 5'-AAACTCATGAGCAGTCTGCA-3' | 24 |
|  |  | 5'-AGGAGATCTTCAGTTTCGGAGG-3' | 25 |
| h18s RNA | qRT-PCR | 5'-GCATTCGTATTGCGCCGCTA-3' | 26 |
|  |  | 5'-AGCTGCCCGGCGGGT-3' | 27 |
| IFI16 | qRT-PCR | 5'-ACTGAGTACAACAAAGCCATTTGA-3' | 28 |
|  |  | 5'-TTGTGACATTGTCCTGTCCCCAC-3' | 29 |
| STING | qRT-PCR | 5'-CCTGAGCAGAACAACTGC-3' | 30 |
|  |  | 5'-GGTCTTCAAGCTGCCCACAGT-3' | 31 |

Results are described below.

Figure 1B:
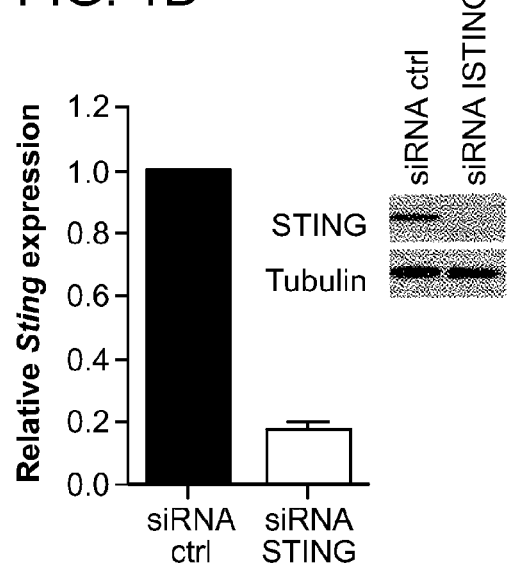
Figure 1C:
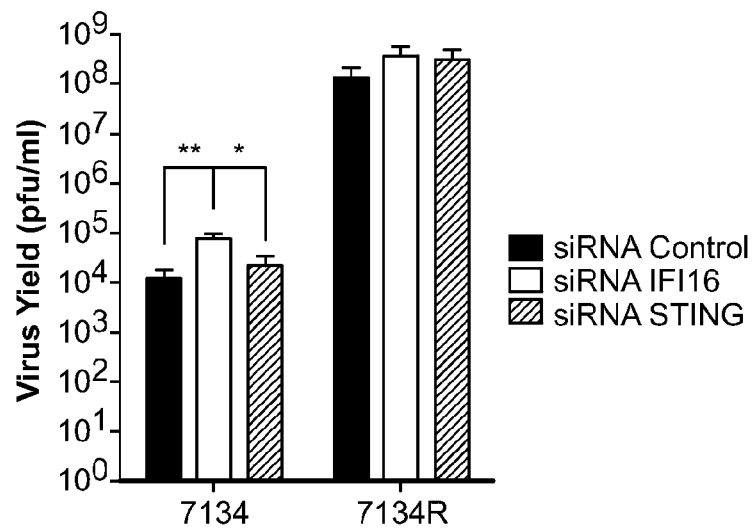

Reduction of IFI16 Enhances ICP0-Null Virus Replication in Normal Human Foreskin Fibroblasts To determine whether IFI16 plays a role in the reduced replication of ICP0-null viruses, normal human foreskin fibroblasts (HFF) were treated with siRNA to reduce IFI16 expression. HFF cells were transfected with siRNA specific for IFI16 (siRNA IFI16) or nontargeting control siRNA (siRNA ctrl). A significant decrease was observed in the expression of IFI16 at both the mRNA and protein level at 72 hours post-transfection (hpt) (FIG. 1A) and knockdown was robust through 120 hpt. siRNA-treated cells were subsequently infected with an ICP0-null virus (7134) or its corresponding rescue (7134R) at a low MOI (0.1), and virus yields were determined by plaque assay. At 48 hpi a ~4 log defect in 7134 virus replication was observed compared to 7134R in control-treated cells (FIG. 1C). While a minimal increase in 7134R virus yield was seen in IFI16 siRNA-treated cells, replication of the 7134 virus was significantly increased (seven-fold) in the absence of IFI16. These results indicated that IFI16 restricts HSV-1 replication in the absence of ICP0 and that the IFI16 protein accounts for a portion of the attenuated ICP0-null phenotype seen in human fibroblasts.

Figure 1D:
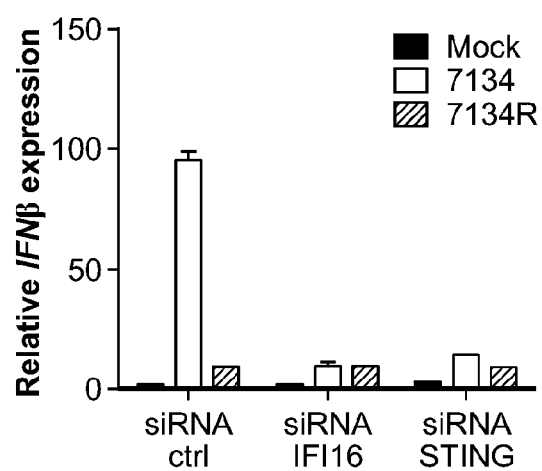

Fibroblasts infected with ICP0-null viruses show enhanced expression of type I interferons and interferon-stimulated genes (ISGs) compared to wild-type viruses (FIG. 1D). The induction of these antiviral genes are, at least in part, due to nuclear sensing of viral DNA by IFI16.

Therefore, it was possible that the increased replication of 7134 observed in the virus yield assay was due to the down regulation of IFI16-induced antiviral genes (FIG. 1D). Studies were then conducted to evaluate the involvement of these pathways in ICP0-null virus replication by examining virus yields in the absence of stimulator of interferon genes (STING). This protein is an adaptor in intracellular DNA sensing and decreased expression of STING greatly inhibits IRF-3 activation and type I interferon induction in response to HSV. Knockdown of STING (FIG. 1B) increased the replication of 7134 and 7134R by 1.8 and 2.2 fold (FIG. 1D), respectively, confirming that signaling events downstream of STING, including the induction of type I interferons and ISGs, are not involved in the intrinsic resistance to ICP0-null viruses. Together these results indicated that IFI16 acts to restrict viral gene expression independently of STING and its role in IRF-3 signaling.

Knockdown of IFI16 Enhances HSV-1 Immediate-Early Gene Expression

Figure 2A:
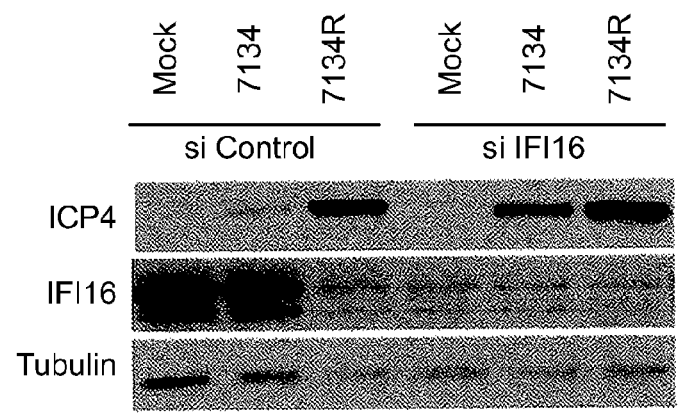
FIGS. 2A-B are immunoblots showing that reducing IFI16 protein levels increases the expression of a viral immediate-early protein. Immunoblot assays were used to examine the levels of the HSV-1 ICP4 immediate early protein in HFF cells treated with IFI16 or non-targeting control siRNA. Treated cells were either mock-infected or infected with an ICP0-null (7134) or rescued virus (7134R) at an MOI of 10. Total whole cell lysates were harvested and probed at (A) 6 and (B) 24 hpi. The cellular tubulin gene was used as a recovery and loading control.
Figure 2B:
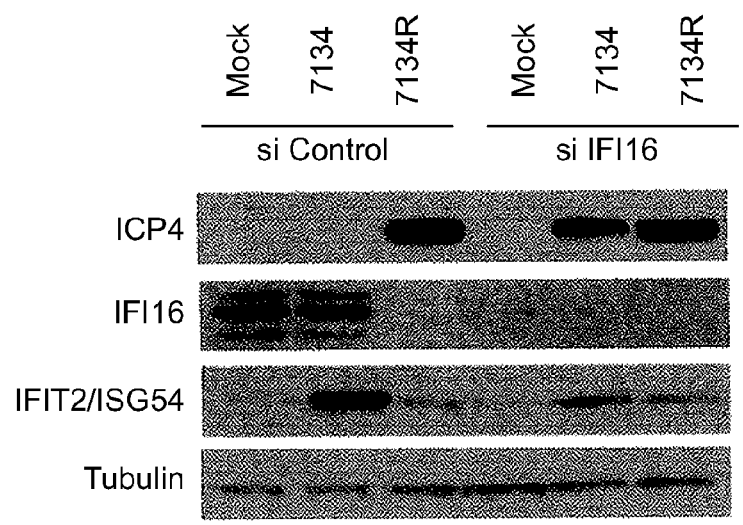

The experiments above showed that IFI16 can restrict ICP0-null virus replication and spread; however, it was unclear what stage in the viral lifecycle is inhibited by IFI16. To investigate the mechanism(s) of IFI16-mediated inhibition of viral replication, the expression of the viral ICP4 immediate-early gene during infection of siRNA-treated cells was examined. HFF cells were transfected with IFI16 siRNA or non-target control siRNA, infected with 7134 or 7134R at an MOI of 10, and whole cell lysates were harvested at 6 or 24 hpi. Western blot analysis revealed an increase in the expression of ICP4 in 7134-infected IFI16 knockdown cells (FIGS. 2A-B), compared to control-treated cells at both time points, consistent with the increase in viral replication observed in FIG. 1C. There was not an increase in ICP4 expression during infection with 7134R, consistent with ICP0 overcoming IFI16-mediated inhibition by promoting the proteasomal degradation of IFI16. Together these results indicate that IFI16 inhibits HSV-1 replication early during infection at the stage of immediate-early gene expression.

Knockdown of IFI16 Enhances Plasmid DNA Expression

Figure 3A:
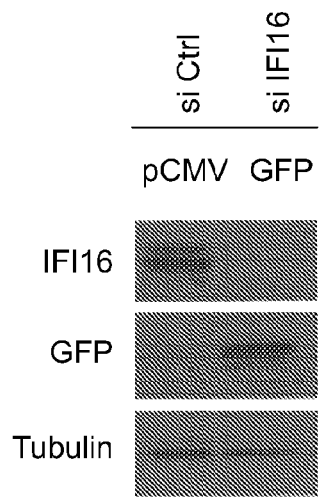
FIG. 3A is an immunoblot and FIG. 3B is a bar graph showing that IFI16 restricts plasmid DNA expression in a promoter-independent manner. (A) Immunoblot examining GFP and IFI16 expression in pCMV GFP transfected human foreskin fibroblasts (HFF) treated with non-targeting control or IFI16 siRNA. The cellular tubulin gene was used as a recovery and loading control. (B) Quantification of GFP cells in the presence or absence of IFI16 by flow cytometry. HFF were transfected with an empty vector plasmid or pCMV GFP or pEF1 GFP at 48 hours post siRNA treatment. The results are represented as a % of the GFP signal from empty vector transfected cells and are an average of two-independent experiments.
Figure 3B:
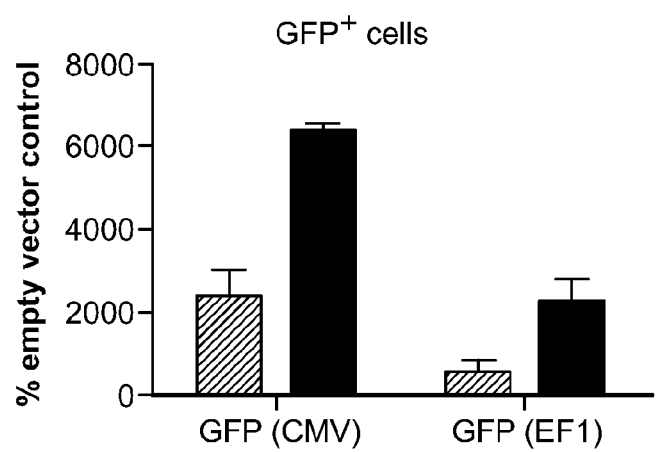

Studies were then carried out to ask whether this repressive effect of IFI16 was also exerted on transfected DNA by testing whether IFI16 could restrict gene expression from plasmid DNA. HFF were treated with IFI16 or control siRNA and transfected with a GFP construct under the control of a CMV promoter (pCMV GFP) at 48 hours post-siRNA treatment. Whole cell lysates were harvested at 24 hpt and GFP protein levels were examined by western blot. An increase in GFP expression in siIFI16 treated cells was observed compared to control cells (FIG. 3A). This increase was quantified by measuring GFP by flow cytometry and we observed a three-fold increase in GFP cells in the absence of IFI16 (FIG. 3B).

To determine whether this response was specific to the viral CMV promoter used to express the GFP plasmid above, GFP expression from a plasmid under the control of the endogenous elongation factor 1 (EF1) promoter was evaluated. While the efficiency of transfection was lower in control cells transfected with pEF1 GFP compared to pCMV GFP transfected cells, a similar increase in GFP cells was observed in the absence of IFI16 (FIG. 3B). Together these results indicate that IFI16 inhibits foreign DNA expression regardless of whether the DNA is introduced to cells by infection or transfection and is not specific to DNA that contains viral promoter elements. Thus, the methods to reduce or inhibit IFI16 expression and/or activity are applicable as an adjunct to any gene expression system to increase efficiency and yield of the desired gene product.

Figure 9:
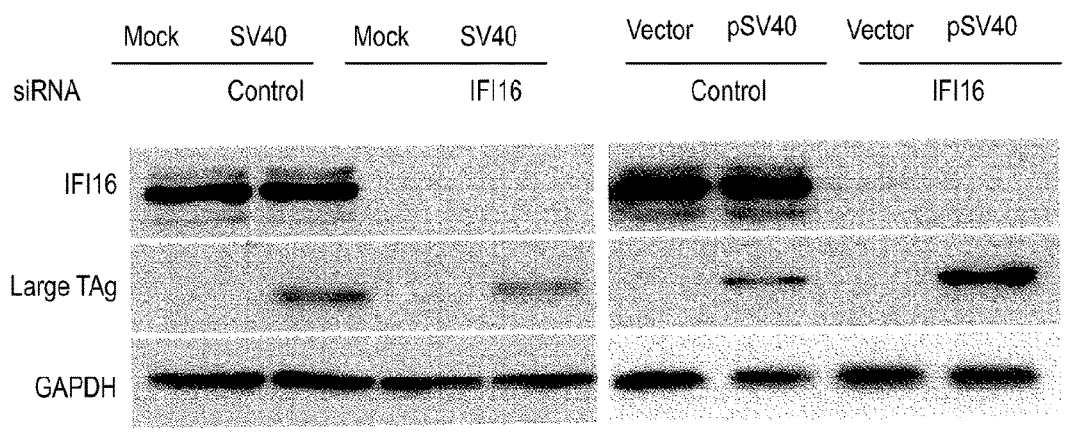
FIG. 9 is a photograph of an electrophoretic gel showing the effect of IFI16 on transfected and SV40 DNA. siRNA-transfected HFF were infected with WT SV40 (MOI of 0.1) or transfected with pSV40 (0.5 µg). Cell lysates were prepared at 48 h posttreatment and analyzed by Western blot for TAg protein levels. IFI16 depletion was confirmed by Western analysis, and the cellular GAPDH gene was used as a recovery and loading control (*$P<0.05$ and **$P<0.01$, Student t test).
Figure 10A:
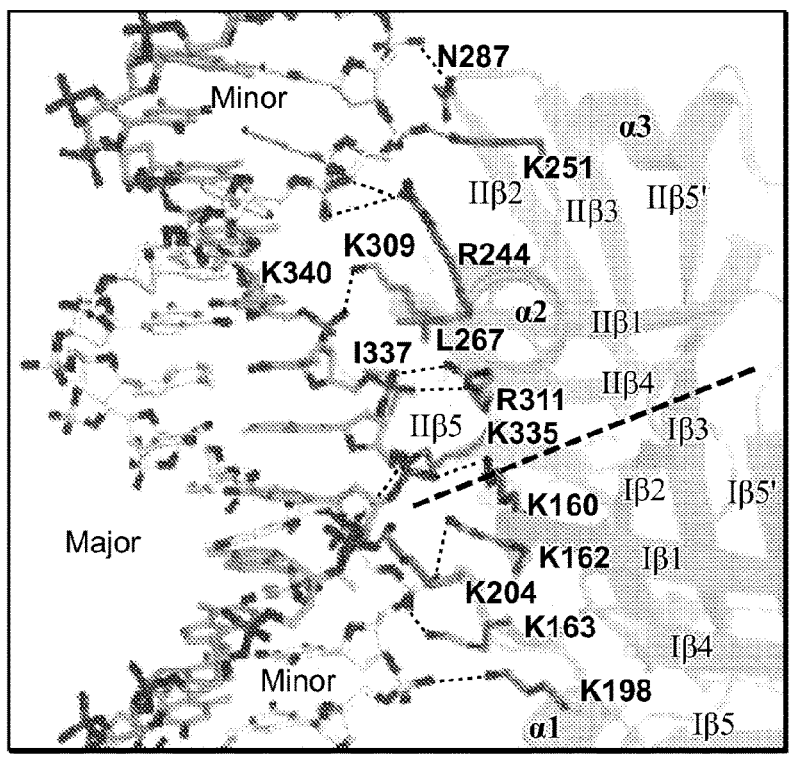
FIGS. 10A-B are diagrams showing HIN:DNA interactions.
Figure 10B:
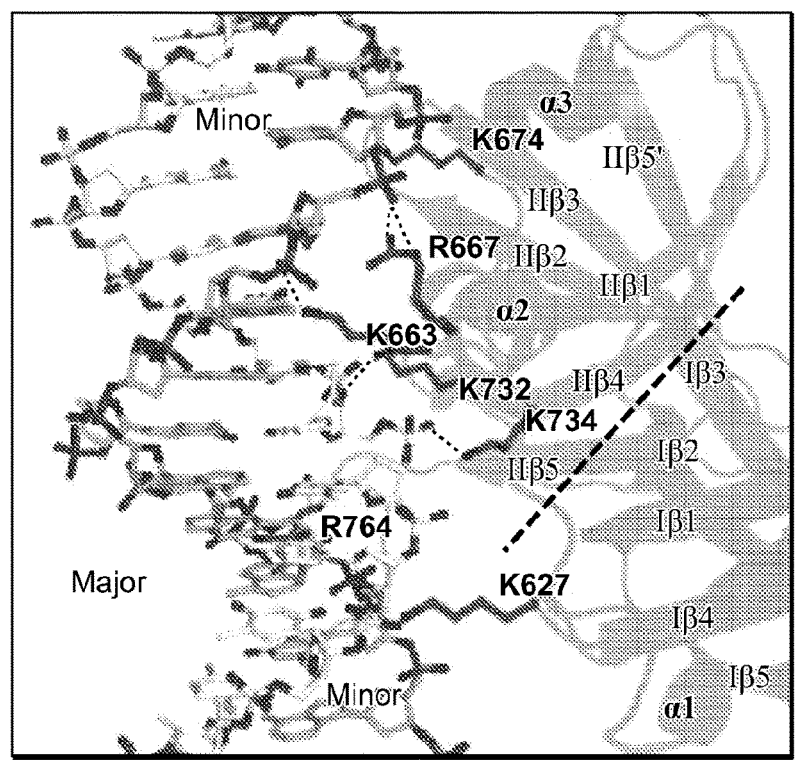
Figure 10C:
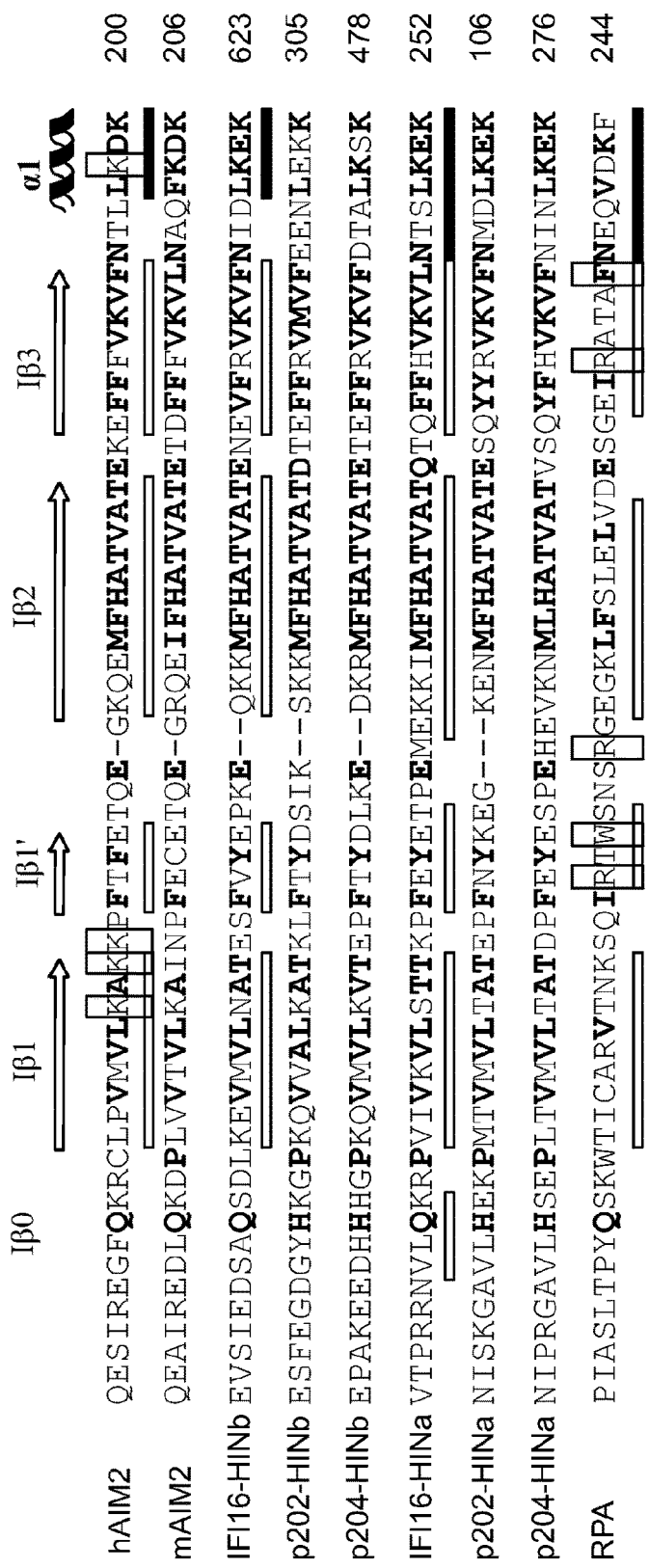
FIG. 10C is a diagram of a sequence alignment of HIN domains. These figures show that HIN Domains bind both strands of the dsDNA. (A) Detailed HIN:DNA interactions for the AIM2 HIN:DNA complex. The hydrogen bonds are indicated as dotted lines. Secondary structures for the AIM2 HIN domain are labeled. The approximate boundaries of the OB1-OB2 are marked with a dotted line and the major and minor grooves of the dsDNA are marked in gray. (B) Detailed HIN:DNA interactions are shown for the IFI16 HINb:DNA complex. (C) Sequence alignment of the HIN domains. Sequences of selected dsDNA-binding HIN domains from human AIM2 (NP_004824), mouse AIM2 (NP_001013801), human IFI16 (Q16666), mouse p204 (NP_032355, a homolog of human IFI16), mouse p202 (NP_032353, an inhibitor of AIM2), as well as a ssDNA-binding OB superfamily protein RPA (NP_002936) were aligned by ClustalW with minor adjustments. The α helices are shown, and the β strands were underlined and marked with "I" and "II" for OB1 and OB2, respectively. Conserved residues are shaded, and DNA binding residues are in black boxes. SEQ ID NO: 32-40 are shown.
Figure 10C:
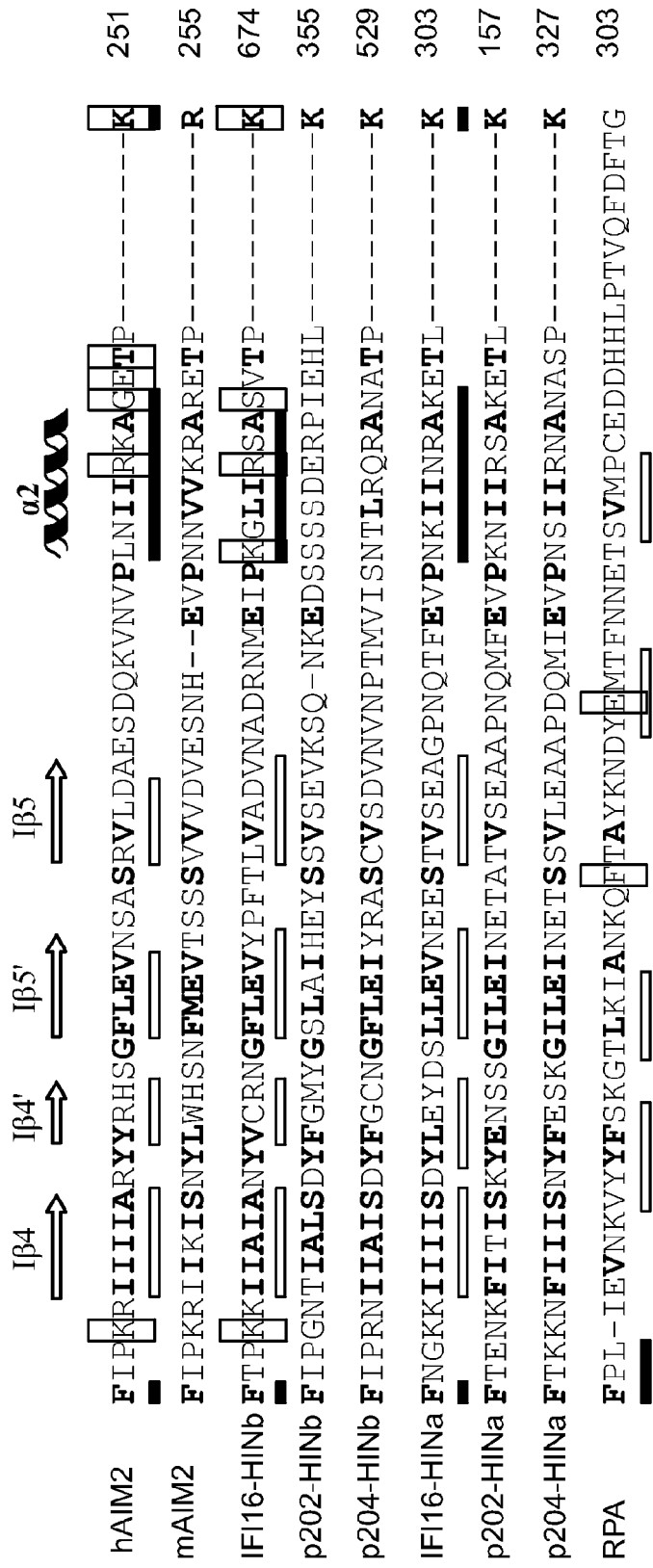
Figure 10C:
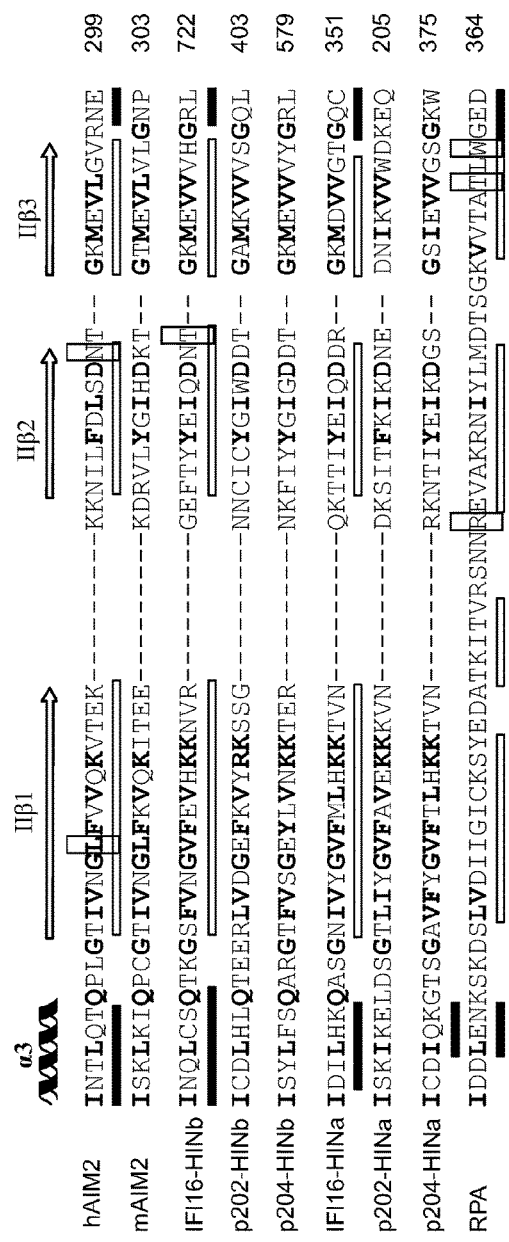
Figure 10C:
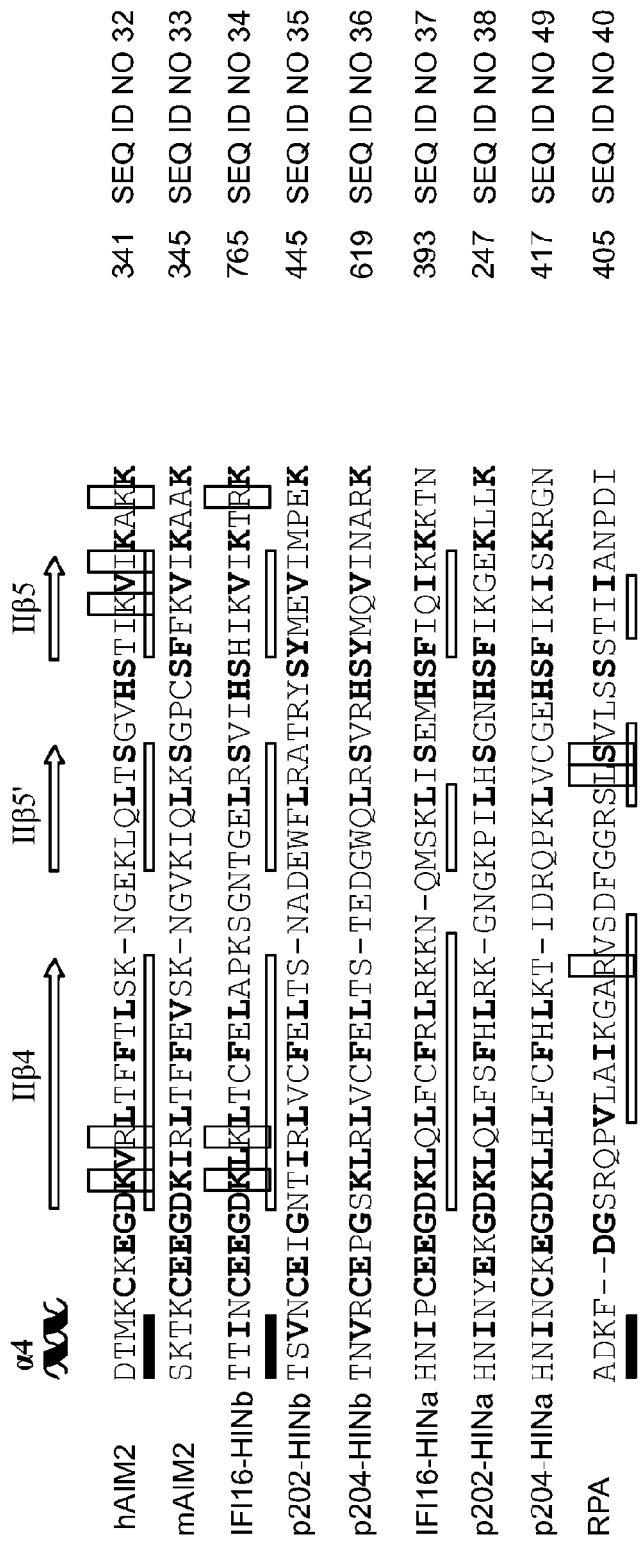
Figure 11:
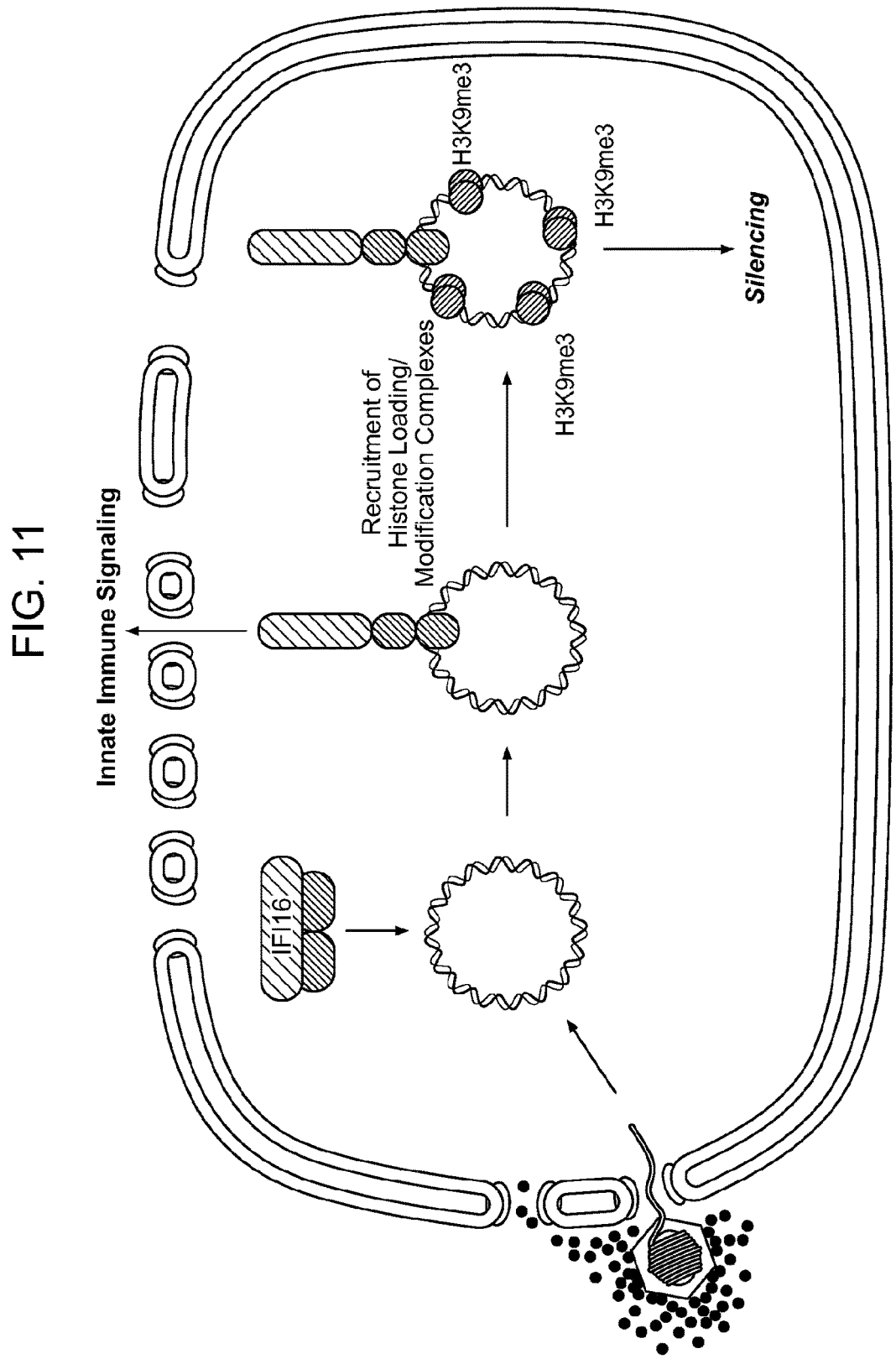
FIG. 11 is a diagram of the mechanism of IFI16 restriction. The diagram depicts IFI16 restriction of HSV gene expression. IFI16 binds to nucleosome-free DNA that accumulates in the nucleus. DNA-bound IFI16 undergoes a conformational change releasing the pyrin domain from an autoinhibited state. Activated IFI16 can signal from the nucleus to the cytoplasm to activate innate immune signaling pathways and recruit chromatin modification complexes that promote H3K9me3 on viral genomes, resulting in gene silencing.

To test whether additional DNA viruses are affected by IFI16, the expression of large T antigen (TAg) during simian virus 40 (SV40) infection or GFP expression from an adenovirus vector (Ad5-GFP) in the presence or absence of IFI16 was examined. At 48 hpi, there was no difference in the accumulation of TAg in IFI16-depleted cells infected with SV40 (MOI of 0.1) compared with control cells (FIG. 9). Similarly, there was no increase in GFP+ cells during Ad5-GFP infection. However, when cells were transfected with a plasmid encoding the WT SV40 genome (pSV40), an increase in the accumulation of TAg in the absence of IFI16 was observed (FIG. 9), indicating that IFI16 was capable of restricting SV40 gene expression from DNA introduced as a plasmid. The apparent lack of an effect on virion-delivered DNA suggested that the genomes within SV40 and adenovirus virions are resistant to the IFI16 effect. These results suggested that IFI16 targets exogenous DNA not associated with nucleosomes and that the SV40 genome in the virion, which contains nucleosomes, is resistant to the restriction effect of IFI16. Similarly, the adenoviral genome in the virion is associated with core protein VII, which prevents IFI16 binding.

Prior to the invention, efforts to increase gene expression included increasing the amount of DNA delivered to the cell and/or increasing the strength of the promoter (inserting the DNA into a vector under the control of a strong promoter). The compositions and methods described herein offer several advantages compared to those earlier systems. The methods involved reducing/decreasing a process that inhibits gene expression in normal cells; thus, it has wide compatibility with any gene expression system. IFI16 inhibition also permits using less virus/viral vector to obtain greater levels of gene expression leading to more production of the desired gene product.

Figure 4A:
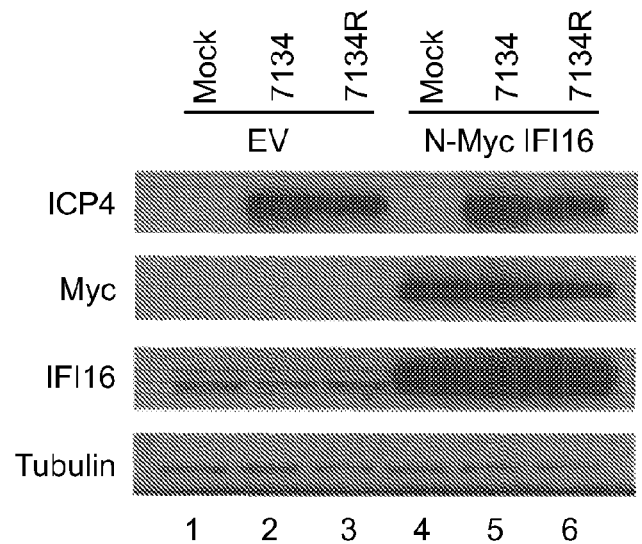
FIGS. 4A-B are immunoblots showing the effect of IFI16 overexpression on U2OS cell permissivity. Expression of exogenous IFI16 resulted in the decreased expression the viral ICP4 immediate-early gene. U2OS cells were transfected with either an empty vector control or an N-terminally Myc-tagged IFI16 construct. At 48 hpt, cells were infected with an ICP0-null (7134) or rescued virus (7134R) at an MOI of (A) 10, or (B) 0.1. Whole cell lysates were harvested and subjected to Western blot analysis for ICP4, Myc, and IFI16 protein levels at 4 hpi. The cellular tubulin gene was used as a recovery and loading control.
Figure 4B:
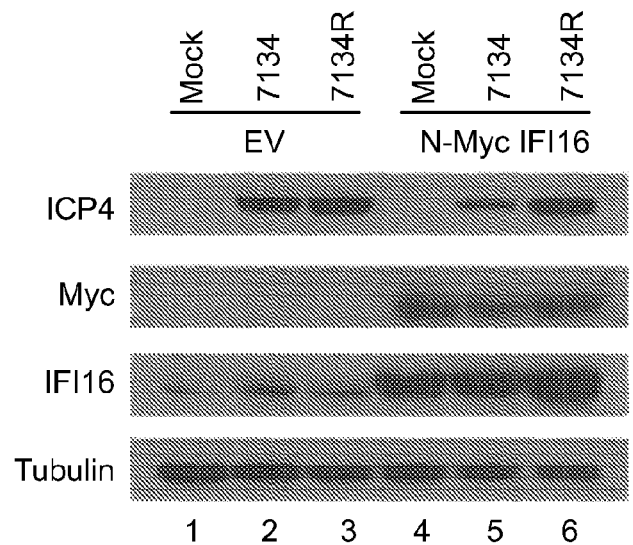

Overexpression of IFI16 in a Permissive Cell Line Reduces ICP0-Null Virus Gene Expression HSV-1 mutants deficient in functional ICP0 are grown on the osteosarcoma U2OS cell line due to an intrinsic ability of these cells to complement ICP0-null viruses. Due to the observation that IFI16 restricts HSV-1 gene expression in HFF, studies were carried out to determine whether IFI16 is present and/or functional in U2OS cells. IFI16 was detected by western blot in U2OS cells (FIG. 4A, lane 1); however, in contrast to observations in HFF, infection with 7134R virus at an MOI of 10 did not result in the degradation of IFI16 in these cells (FIG. 4.4A, lane 3). Interestingly, an inability of ICP0 to degrade IFI16 in additional cell lines, including HeLa and Hep2 cells was observed. Nevertheless, exogenous IFI16 introduced to U2OS cells by transfection was degraded during infection with the 7134R virus (FIG. 4A, lane 6), suggesting that endogenous IFI16 in U2OS cells may be mutated or modified in some way that prevents ICP0 from promoting its degradation. The ability of ICP0 to target exogenous IFI16 in U2OS cells indicated the protein might be capable of restricting ICP0-null virus gene expression. In FIG. 4A, no difference was observed in the steady-state levels of ICP4 during infection with 7134 in the absence or presence of N-Myc IFI16 (lane 2 vs lane 5). However, this experiment was performed at an MOI of 10 to maximize the ability to detect ICP0-dependent degradation of IFI16. Defects in ICP0-null virus gene expression are more apparent at low MOI, so the expression of ICP4 was examined during infection at an MOI of 0.1. U2OS cells were transfected with an empty vector plasmid or N-Myc IFI16 for 48 h, infected with 7134 and 7134R, and whole cell lysates were harvested at 4 hpi. In contrast to our results at a high MOI of infection, expression of N-Myc IFI16 was associated with a decrease in ICP4 expression in low MOI 7134-infected cells compared to the empty vector control (FIG. 4B, lane 2 vs lane 5). Consistent with its specificity for ICP0-null viruses, there was not a decrease ICP4 expression in the presence of N-Myc IFI16 during infection with 7134R (FIG. 4B, lane 3 vs lane 6). Together these results provide further evidence of IFI16's activity as an intrinsic resistance factor to ICP0-null virus infection. Furthermore, the results indicate that endogenous IFI16 in U2OS cells is non-functional and accounts for at least a portion of this cell lines apparent permissivity to ICP0-null virus replication.

Knockdown of IFI16 does not Affect PML Recruitment to Viral Genomes

Figure 5A:
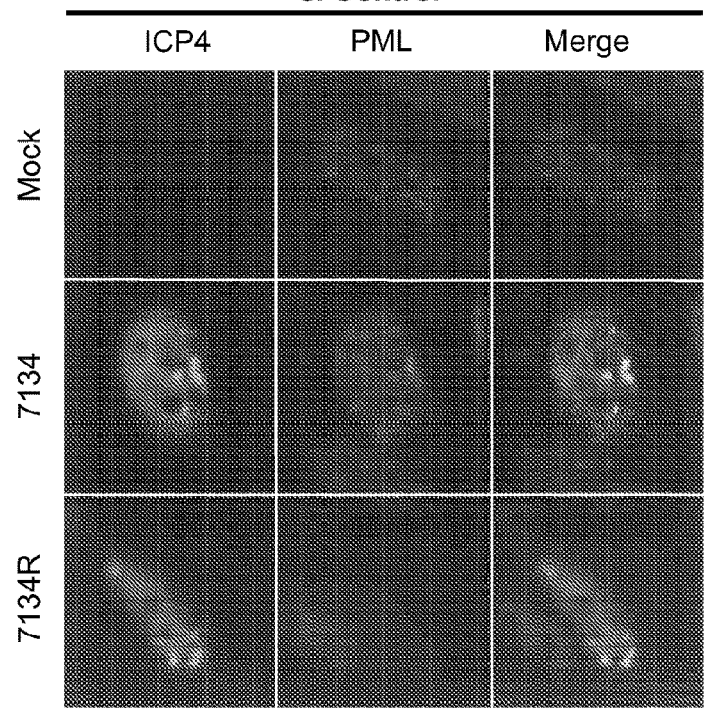
FIGS. 5A-B are photomicrographs showing that the ND10 component PML is recruited to sites associated with viral genomes in the absence of IFI16. Immunofluorescence of non-targeting control or IFI16 siRNA transfected HFF infected with HSV-1. HFF were treated with indicated siRNA for 72 hours prior to infection with an ICP0-null (7134) or rescued virus (7134R) at an MOI of 1 or 0.001, respectively. Cells were fixed and simultaneously stained at 24 hpi with mouse anti-ICP4 and rabbit anti-PML antibodies followed by Alexa Fluor 488 goat anti-mouse and Alexa Fluor 594 goat-anti rabbit secondary antibodies.
Figure 5B:
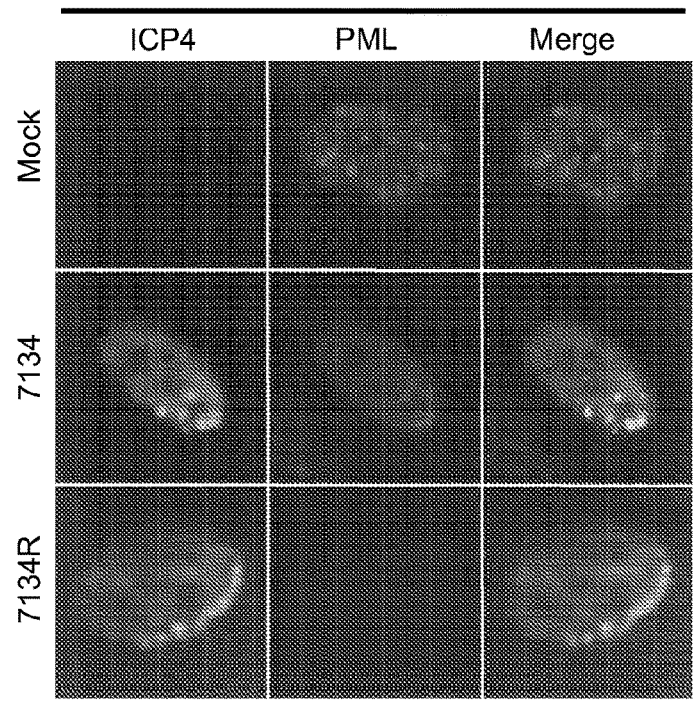

During the cellular response to HSV-1 infection, components of ND10 bodies accumulate at sites adjacent to viral DNA, which correlates with their involvement in the repression of viral replication. This accumulation is observed during infection with ICP0-null viruses, as wild-type virus infection overcomes ND10-mediated repression by targeting components of these domains for degradation in an ICP0-dependent manner. IFI16 has not been identified as an ND10 component, nor does it localize to nuclear foci that would be indicative of this domain in normal human foreskin fibroblasts. However, given the involvement of IFI16 in the restriction of viral gene expression, studies were carried out to ask whether the protein is involved in the recruitment of ND10 components to viral genomes. To answer this question, a technique for analyzing ND10 accumulation at sites of viral DNA entry into the nucleus was used. This assay involves imaging cells along the edge of a viral plaque, where incoming viral genomes accumulate asymmetrically in the cell nucleus. HFF were treated with control siRNA or IFI16 siRNA to decrease IFI16 expression. Cells were then infected with 7134 (MOI 1) or 7134R (MOI 0.001) and fixed at 24 hours post-infection. Infection with 7134 at the higher MOI was necessary to observe plaque formation on HFF as ICP0-null viruses have up to a three-log defect in plaque forming efficiency on human fibroblasts. Incoming viral genomes were visualized with an antibody specific for the viral ICP4 immediate-early protein, which has previously been shown to co-localize with viral DNA, and PML was used as a marker for ND10. No difference was observed in the accumulation of PML at ICP4 foci in 7134-infected IFI16-knockdown cells compared to control cells, and PML was degraded in 7134R-infected cells irrespective of knockdown (FIGS. 5A-B). Furthermore, hDaxx was also recruited to genome complexes in the absence of IFI16, indicating that this phenotype could be generalized to other ND10 components. Together these results demonstrated that the IFI16-mediated restriction of an ICP0-null mutant is not due to a disruption in ND10 activity.

IFI16 Plays a Broad Role in the Sensing and Silencing of Foreign DNA

During infection viruses are faced with a barrage of cellular intrinsic resistance and innate immune responses aimed to prevent their replication and spread. Herpesviruses, which are highly ubiquitous and can establish lifetime latent infections, robustly counteract these cellular responses through the expression of multiple immunomodulatory proteins. This complexity has hindered the investigation of the host response to these viruses, as gene knockdown approaches (e.g., siRNA) rarely provide robust phenotypic information when infecting with wild-type-viruses that modulate the pathways investigated. Therefore, to study the cellular responses to these large DNA viruses, one must use recombinant mutant viruses that do not express known immunomodulatory proteins. In the case of HSV-1, the viral ICP0 immediate-early protein has been shown to inhibit both intrinsic resistance and innate immune responses to viral infection. Previous studies using ICP0-null viruses have revealed that one major cellular response to DNA virus infection involves the silencing of incoming viral genomes, and while nuclear ND10 have been implicated in partially mediating this host response, other factors were not known.

The data described above established that the nuclear IFI16 DNA sensor is involved in the intrinsic cellular response to HSV-1 infection, as demonstrated by the increased expression and replication of an ICP0-null virus in the absence of IFI16. The data revealed that IFI16 did not affect the recruitment of ND10 components to viral genomes, indicating the intrinsic activity of IFI16 is independent of a previously described DNA silencing response. The complementation of the 7134 virus upon knockdown of IFI16 was similar to the remaining 10-fold inhibition observed in human fibroblasts when several ND10 components were simultaneously decreased by shRNA expression, indicating that IFI16 plays a role in the silencing of incoming genomes. The results presented indicate that in addition to its involvement as an innate pattern recognition receptor, IFI16 plays a broader role in the sensing and silencing of foreign DNA as a mediator of intrinsic cellular resistance.

IFI16 is Involved in Recruiting Chromatin Remodeling Complexes and/or Histones to Foreign DNA.

Figure 6A:
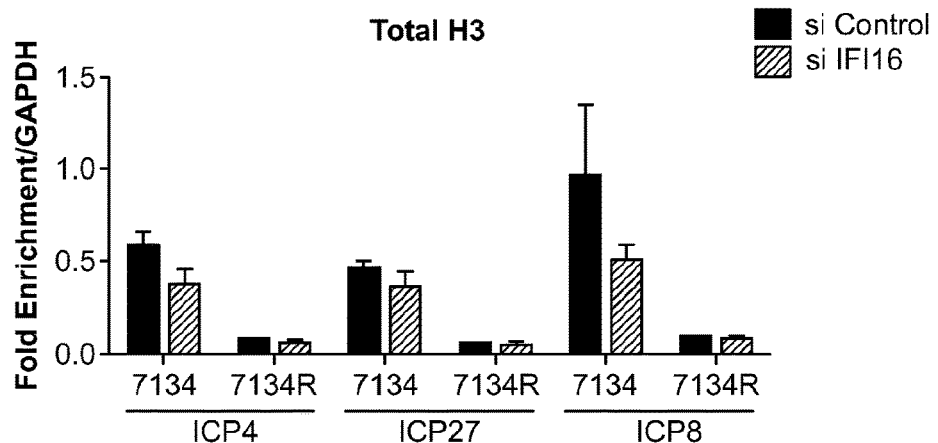
FIGS. 6A-C are bar graphs showing chromatin association with viral DNA in the absence of IFI16.
Figure 6B:
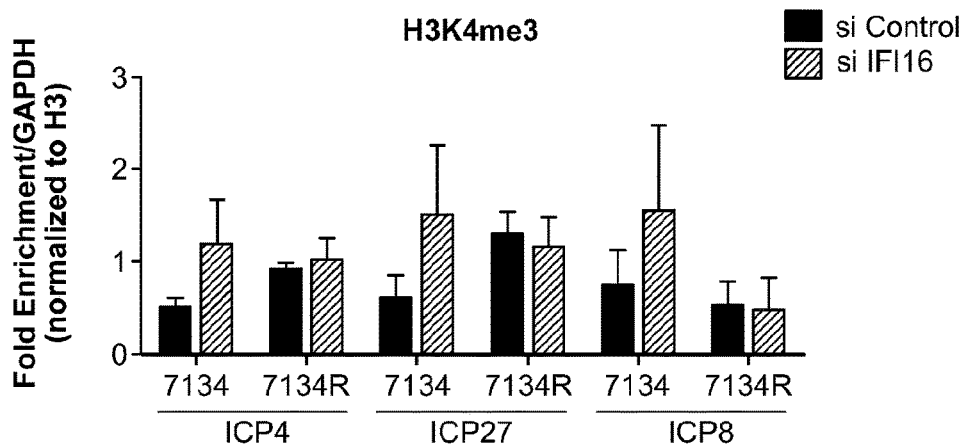
Figure 6C:
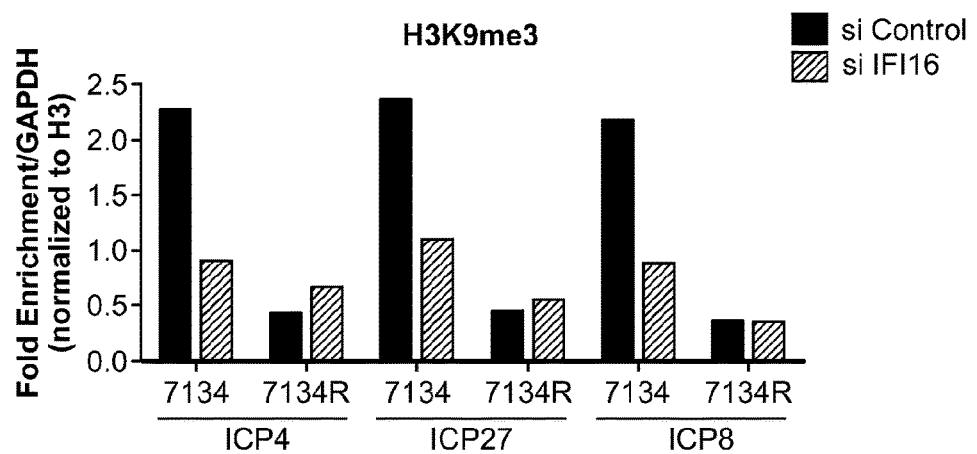
Figure 7:
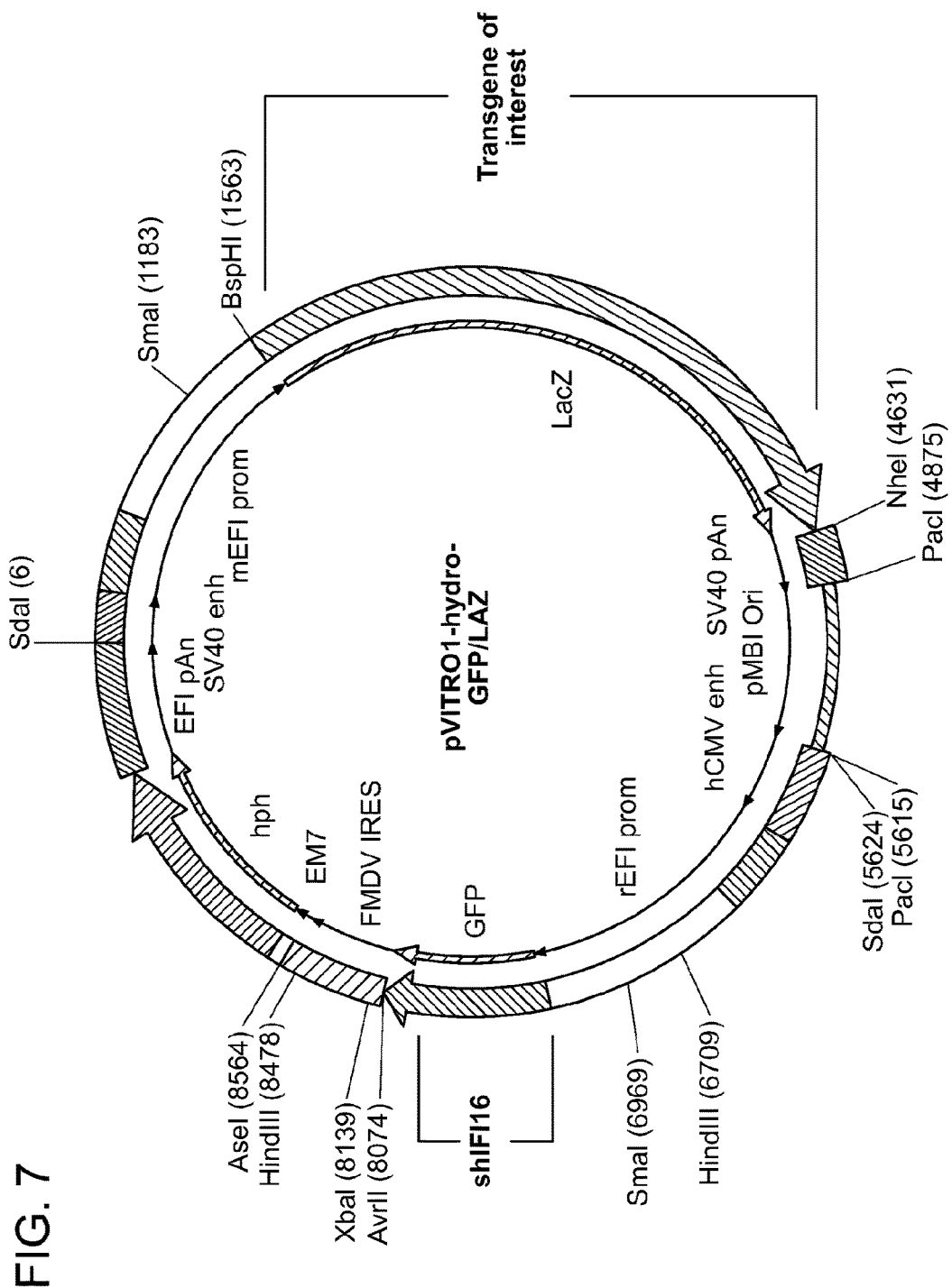
FIG. 7 is a diagram of a vector map of an example of a modified dual promoter vector that is used to express an IFI16 shRNA and a transgene of interest.

Knockdown of IFI16 enhances euchromatin and reduces heterochromatin on viral DNA. HFF treated with IFI16 or control siRNA were infected with an ICP0-null (7134) or rescued virus (7134R) at an MOI of 1. Cells were fixed at 6 hpi and sonicated chromatin was immunoprecipitated with (A) anti-H3, (B) anti-H3K4me3, (C) anti-H3K9me3 or rabbit IgG antibodies (see FIGS. 6A-C). Immunoprecipitated DNA was measured by real-time PCR using primers for the ICP27, ICP4 and ICP8 genes. Data are presented as the percentage of the DNA immunoprecipitated with background signal from the normal rabbit IgG subtracted followed by normalization to the fraction of immunoprecipitated GAPDH DNA.

Figure 8A:
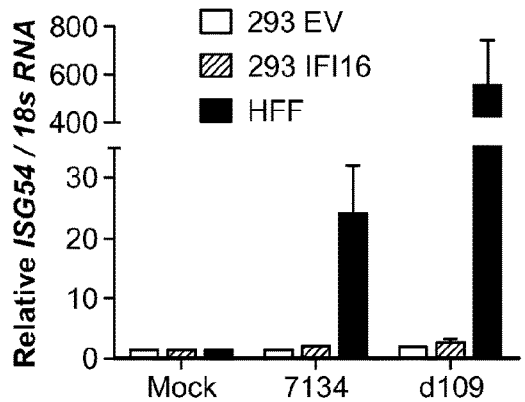
FIGS. 8A, B and D are bar graphs
Figure 8B:
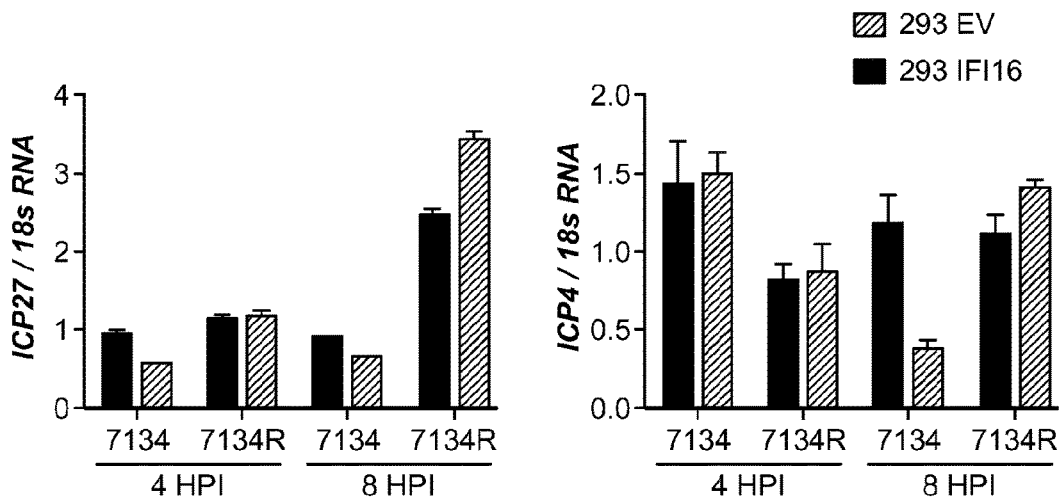
FIG. 8C is a photographs of a Western blot assay. These figures show that stable expression of IFI16 in HEK293 cells inhibits viral gene expression and replication independently of IRF-3 activation. (A) Control HEK293 cells (293 EV), HEK293 cells stably expressing IFI16 (293 IFI16), or HFFs were infected with 7134 or d109 viruses. Total cell-associated RNA was harvested at 6 hpi and prepared for qRT-PCR. ISG54 transcripts were normalized to 18S RNA and made relative to mock-infected cells. (B) Total RNA was harvested at 4 or 8 hpi and analyzed by qRT-PCR for ICP4 and ICP27 mRNA. Transcripts were normalized to 18S RNA. (C) Cell lysates were harvested at 6 hpi and analyzed by Western blot for ICP4, IFI16, and Tubulin levels. (D) Virus yields at 24 hpi were determined by plaque assay on U2OS cells. Cells were infected with an MOI of 10 for A and an MOI of 0.1 for B-D.
Figure 8C:
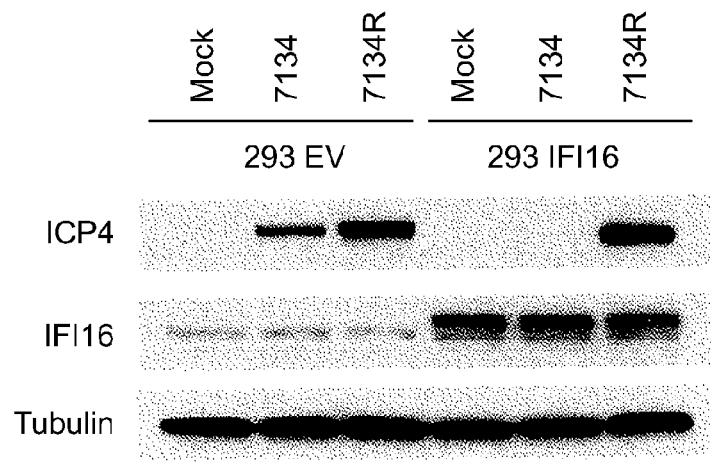
Figure 8D:
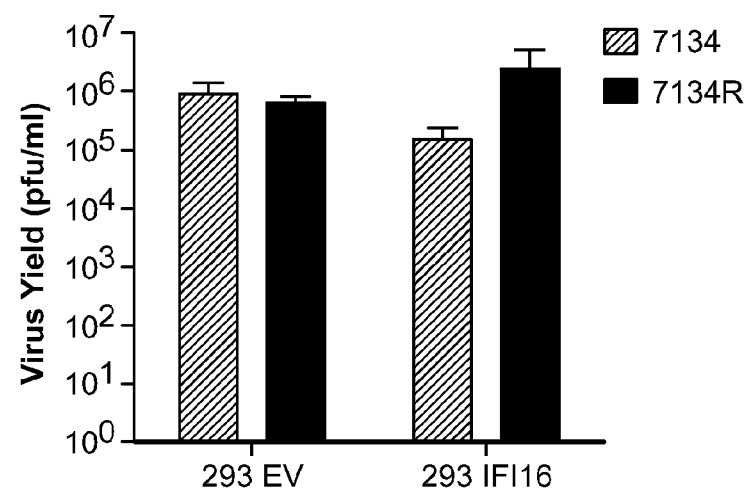

Stable Expression of IFI16 in HEK293 Cells Inhibits Viral Gene Expression and Replication Independently of IRF-3 Activation Infection of these cells with 7134 virus resulted in a reduction in ICP4 and ICP27 mRNA and protein levels (FIGS. 8B and C) and virus yields (FIG. 8D) relative to vector control cells. Overexpression of IFI16 in HEK293 cells did not result in a rescue of these cells to induce ISG54 expression in response to HSV infection (FIG. 8A). Together these results provided further evidence of IFI16's activity as an intrinsic resistance factor and indicate that, even though expression of IFI16 is sufficient to restrict viral gene expression, it is not sufficient to induce an innate immune response in these cells, further arguing that these activities of IFI16 are separable. Furthermore, the results indicated that endogenous IFI16 in U2OS cells is nonfunctional and accounts for this cell line's permissivity for ICP0-null virus replication.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method of augmenting expression of a heterologous nucleic acid in a eukaryotic cell comprising:
   (a) decreasing expression or activity of endogenous Interferon-induced protein-16 (IFI16) in the cell; and
   (b) expressing a heterologous nucleic acid in the cell of step (a), wherein said heterologous nucleic acid comprises a viral vector comprising a non-viral or viral coding sequence;
   wherein the steps of (a) and (b) do not occur at the same time.

2. The method of claim 1, wherein said heterologous nucleic acid coding sequence comprises non-viral DNA.

3. The method of claim 1, wherein said heterologous nucleic acid coding sequence encodes a mammalian gene product.

4. The method of claim 1, wherein an IFI16 protein is encoded by a nucleic acid comprising the sequence of SEQ ID NO:5.

5. The method of claim 1, wherein an IFI16 protein comprises the amino acid sequence of SEQ ID NO:1, 2, 3, or 4.

6. The method of claim 1, wherein said expression is decreased by contacting said cell with an IFI16-specific siRNA.

7. The method of claim 6, wherein said IFI16-specific siRNA is selected from the group consisting of GAUCUGUAAUUCAUAGUCA (SEQ ID NO: 6), GGACCAGCCCUAUCAAGAA (SEQ ID NO: 7), GGAGUAAGGUGUCCGAGGA (SEQ ID NO: 8), CAGCGUAACUCCUAAAAUC (SEQ ID NO: 9), and GCUGGUCCUAACCAAACGU (SEQ ID NO: 10).

8. The method of claim 1, wherein said expression is decreased by contacting said cell with an IFI16-specific shRNA.

9. The method of claim 8, wherein said IFI16-specific shRNA is selected from the group consisting of

```
#1 Sense:
                                    (SEQ ID NO: 11)
CCACAAUCUACGAAAUUCA, Anti-sense:
                                    (SEQ ID NO: 12)
UGAAUUUCGUAGAUUGUGG;

#2 Sense:
                                    (SEQ ID NO: 13)
CCAUCCAGCAGUUUCUUCA, Anti-sense:
                                    (SEQ ID NO: 14)
UGAAGAAACUGCUGGAUGG;
and

#3 Sense:
                                    (SEQ ID NO: 15)
GGAAGGAGAUAAACUGAAA, Anti-sense:
                                    (SEQ ID NO: 16)
UUUCAGUUUAUCUCCUUCC.
```

10. The method of claim 1, wherein said expression is decreased by contacting said cell with an IFI16-specific antisense nucleic acid.

11. The method of claim 1, wherein said activity is decreased by contacting said cell with an inhibitor of IFI16 binding to DNA.

12. The method of claim 11, wherein said inhibitor binds to a HIN domain of IFI16.

13. The method of claim 11, wherein said inhibitor binds to residues K663, R667, K732, K734, K759, and/or R764 of IFI16 isotype A or a corresponding residue of isotype B or C.

14. The method of claim 6, wherein said IFI16-regulating nucleic acid sequence comprises an IFI16-specific shRNA.

15. The method of claim 8, wherein said inhibitor reduces binding of IFI16 to heterologous DNA or reduces IFI16-mediated addition of silencing chromatin to said heterologous DNA.

16. The method of claim 3, wherein the eukaryotic cell is a mammalian cell.

17. The method of claim 16, wherein the mammalian cell is a human cell.

18. The method of claim 16, wherein the mammalian gene product is a different form of a protein than is present in the mammalian cell.

19. The method of claim 18, wherein the protein that is present in the mammalian cell is functionally defective.

20. The method of claim 18, wherein the protein that is present in the mammalian cell is non-functional.

21. The method of claim 18, wherein the mammalian gene product is a normal, functionally active protein.

22. The method of claim 16, wherein the mammalian gene product is from a different cell type compared to the mammalian cell.

23. The method of claim 16, wherein the mammalian gene product is from a different species compared to the mammalian cell.

24. The method of claim 1, wherein the mammalian gene product is naturally expressed by the eukaryotic cell.

* * * * *

UNITED STATES PATENT AND TRADEMARK OFFICE
CERTIFICATE OF CORRECTION

| | | |
|---|---|---|
| PATENT NO. | : 10,294,480 B2 | Page 1 of 1 |
| APPLICATION NO. | : 14/888853 | |
| DATED | : May 21, 2019 | |
| INVENTOR(S) | : Knipe et al. | |

It is certified that error appears in the above-identified patent and that said Letters Patent is hereby corrected as shown below:

In the Specification

At Column 1, under the heading GOVERNMENT SUPPORT:
"This invention was made with Government support under contract numbers AI83215 and AIO99081 awarded by the National Institutes of Health. The Government has certain rights in the invention."

Should be replaced with:
— This invention was made with government support under AI099081, AI083215, and AI106934 awarded by the National Institutes of Health. The government has certain rights in the invention. —

Signed and Sealed this
Twelfth Day of May, 2020

Andrei Iancu
*Director of the United States Patent and Trademark Office*

SEQUENCE LISTING

```
<160> NUMBER OF SEQ ID NOS: 40

<210> SEQ ID NO 1
<211> LENGTH: 729
<212> TYPE: PRT
<213> ORGANISM: Homo sapiens

<400> SEQUENCE: 1

Met Gly Lys Lys Tyr Lys Asn Ile Val Leu Leu Lys Gly Leu Glu Val
1               5                   10                  15

Ile Asn Asp Tyr His Phe Arg Met Val Lys Ser Leu Leu Ser Asn Asp
            20                  25                  30

Leu Lys Leu Asn Leu Lys Met Arg Glu Glu Tyr Asp Lys Ile Gln Ile
        35                  40                  45

Ala Asp Leu Met Glu Glu Lys Phe Arg Gly Asp Ala Gly Leu Gly Lys
    50                  55                  60

Leu Ile Lys Ile Phe Glu Asp Ile Pro Thr Leu Glu Asp Leu Ala Glu
65                  70                  75                  80

Thr Leu Lys Lys Glu Lys Leu Lys Val Lys Gly Pro Ala Leu Ser Arg
                85                  90                  95

Lys Arg Lys Lys Glu Val His Ala Thr Ser Pro Ala Pro Ser Thr Ser
            100                 105                 110

Ser Thr Val Lys Thr Glu Gly Ala Glu Ala Thr Pro Gly Ala Gln Lys
        115                 120                 125

Arg Lys Lys Ser Thr Lys Glu Lys Ala Gly Pro Lys Gly Ser Lys Val
    130                 135                 140

Ser Glu Glu Gln Thr Gln Pro Pro Ser Pro Ala Gly Ala Gly Met Ser
145                 150                 155                 160

Thr Ala Met Gly Arg Ser Pro Ser Pro Lys Thr Ser Leu Ser Ala Pro
                165                 170                 175

Pro Asn Ser Ser Ser Thr Glu Asn Pro Lys Thr Val Ala Lys Cys Gln
            180                 185                 190

Val Thr Pro Arg Arg Asn Val Leu Gln Lys Arg Pro Val Ile Val Lys
        195                 200                 205

Val Leu Ser Thr Thr Lys Pro Phe Glu Tyr Glu Thr Pro Glu Met Glu
    210                 215                 220

Lys Lys Ile Met Phe His Ala Thr Val Ala Thr Gln Thr Gln Phe Phe
225                 230                 235                 240
```

-continued

His Val Lys Val Leu Asn Thr Ser Leu Lys Glu Lys Phe Asn Gly Lys
              245                 250                 255

Lys Ile Ile Ile Ile Ser Asp Tyr Leu Glu Tyr Asp Ser Leu Leu Glu
        260                 265                 270

Val Asn Glu Glu Ser Thr Val Ser Glu Ala Gly Pro Asn Gln Thr Phe
    275                 280                 285

Glu Val Pro Asn Lys Ile Ile Asn Arg Ala Lys Glu Thr Leu Lys Ile
290                 295                 300

Asp Ile Leu His Lys Gln Ala Ser Gly Asn Ile Val Tyr Gly Val Phe
305                 310                 315                 320

Met Leu His Lys Lys Thr Val Asn Gln Lys Thr Thr Ile Tyr Glu Ile
            325                 330                 335

Gln Asp Asp Arg Gly Lys Met Asp Val Val Gly Thr Gly Gln Cys His
            340                 345                 350

Asn Ile Pro Cys Glu Glu Gly Asp Lys Leu Gln Leu Phe Cys Phe Arg
        355                 360                 365

Leu Arg Lys Lys Asn Gln Met Ser Lys Leu Ile Ser Glu Met His Ser
    370                 375                 380

Phe Ile Gln Ile Lys Lys Lys Thr Asn Pro Arg Asn Asn Asp Pro Lys
385                 390                 395                 400

Ser Met Lys Leu Pro Gln Glu Gln Arg Gln Leu Pro Tyr Pro Ser Glu
            405                 410                 415

Ala Ser Thr Thr Phe Pro Glu Ser His Leu Arg Thr Pro Gln Met Pro
            420                 425                 430

Pro Thr Thr Pro Ser Ser Ser Phe Phe Thr Lys Lys Ser Glu Asp Thr
        435                 440                 445

Ile Ser Lys Met Asn Asp Phe Met Arg Met Gln Ile Leu Lys Glu Gly
    450                 455                 460

Ser His Phe Pro Gly Pro Phe Met Thr Ser Ile Gly Pro Ala Glu Ser
465                 470                 475                 480

His Pro His Thr Pro Gln Met Pro Pro Ser Thr Pro Ser Ser Ser Phe
            485                 490                 495

Leu Thr Thr Leu Lys Pro Arg Leu Lys Thr Glu Pro Glu Glu Val Ser
        500                 505                 510

Ile Glu Asp Ser Ala Gln Ser Asp Leu Lys Glu Val Met Val Leu Asn
    515                 520                 525

Ala Thr Glu Ser Phe Val Tyr Glu Pro Lys Glu Gln Lys Lys Met Phe
    530                 535                 540

His Ala Thr Val Ala Thr Glu Asn Glu Val Phe Arg Val Lys Val Phe
545                 550                 555                 560

Asn Ile Asp Leu Lys Glu Lys Phe Thr Pro Lys Lys Ile Ile Ala Ile
            565                 570                 575

Ala Asn Tyr Val Cys Arg Asn Gly Phe Leu Glu Val Tyr Pro Phe Thr
            580                 585                 590

Leu Val Ala Asp Val Asn Ala Asp Arg Asn Met Glu Ile Pro Lys Gly
        595                 600                 605

Leu Ile Arg Ser Ala Ser Val Thr Pro Lys Ile Asn Gln Leu Cys Ser
    610                 615                 620

Gln Thr Lys Gly Ser Phe Val Asn Gly Val Phe Glu Val His Lys Lys
625                 630                 635                 640

Asn Val Arg Gly Glu Phe Thr Tyr Tyr Glu Ile Gln Asp Asn Thr Gly
            645                 650                 655

```
Lys Met Glu Val Val His Gly Arg Leu Asn Thr Ile Asn Cys Glu
            660                 665                 670

Glu Gly Asp Lys Leu Lys Leu Thr Ser Phe Glu Leu Ala Pro Lys Ser
        675                 680                 685

Gly Asn Thr Gly Glu Leu Arg Ser Val Ile His Ser His Ile Lys Val
        690                 695                 700

Ile Lys Thr Arg Lys Asn Lys Lys Asp Ile Leu Asn Pro Asp Ser Ser
705                 710                 715                 720

Met Glu Thr Ser Pro Asp Phe Phe Phe
                725

<210> SEQ ID NO 2
<211> LENGTH: 785
<212> TYPE: PRT
<213> ORGANISM: Homo sapiens

<400> SEQUENCE: 2

Met Gly Lys Lys Tyr Lys Asn Ile Val Leu Leu Lys Gly Leu Glu Val
1               5                   10                  15

Ile Asn Asp Tyr His Phe Arg Met Val Lys Ser Leu Leu Ser Asn Asp
            20                  25                  30

Leu Lys Leu Asn Leu Lys Met Arg Glu Glu Tyr Asp Lys Ile Gln Ile
        35                  40                  45

Ala Asp Leu Met Glu Glu Lys Phe Arg Gly Asp Ala Gly Leu Gly Lys
    50                  55                  60

Leu Ile Lys Ile Phe Glu Asp Ile Pro Thr Leu Glu Asp Leu Ala Glu
65                  70                  75                  80

Thr Leu Lys Lys Glu Lys Leu Lys Val Lys Gly Pro Ala Leu Ser Arg
                85                  90                  95

Lys Arg Lys Lys Glu Val Asp Ala Thr Ser Pro Ala Pro Ser Thr Ser
            100                 105                 110

Ser Thr Val Lys Thr Glu Gly Ala Glu Ala Thr Pro Gly Ala Gln Lys
        115                 120                 125

Arg Lys Lys Ser Thr Lys Glu Lys Ala Gly Pro Lys Gly Ser Lys Val
    130                 135                 140

Ser Glu Glu Gln Thr Gln Pro Pro Ser Pro Ala Gly Ala Gly Met Ser
145                 150                 155                 160

Thr Ala Met Gly Arg Ser Pro Ser Pro Lys Thr Ser Leu Ser Ala Pro
                165                 170                 175

Pro Asn Ser Ser Ser Thr Glu Asn Pro Lys Thr Val Ala Lys Cys Gln
            180                 185                 190

Val Thr Pro Arg Arg Asn Val Leu Gln Lys Arg Pro Val Ile Val Lys
        195                 200                 205

Val Leu Ser Thr Thr Lys Pro Phe Glu Tyr Glu Thr Pro Glu Met Glu
    210                 215                 220

Lys Lys Ile Met Phe His Ala Thr Val Ala Thr Gln Thr Gln Phe Phe
225                 230                 235                 240

His Val Lys Val Leu Asn Thr Ser Leu Lys Glu Lys Phe Asn Gly Lys
                245                 250                 255

Lys Ile Ile Ile Ile Ser Asp Tyr Leu Glu Tyr Asp Ser Leu Leu Glu
            260                 265                 270

Val Asn Glu Glu Ser Thr Val Ser Glu Ala Gly Pro Asn Gln Thr Phe
        275                 280                 285

Glu Val Pro Asn Lys Ile Ile Asn Arg Ala Lys Glu Thr Leu Lys Ile
    290                 295                 300
```

-continued

```
Asp Ile Leu His Lys Gln Ala Ser Gly Asn Ile Val Tyr Gly Val Phe
305                 310                 315                 320

Met Leu His Lys Lys Thr Val Asn Gln Lys Thr Thr Ile Tyr Glu Ile
            325                 330                 335

Gln Asp Asp Arg Gly Lys Met Asp Val Val Gly Thr Gly Gln Cys His
        340                 345                 350

Asn Ile Pro Cys Glu Glu Gly Asp Lys Leu Gln Leu Phe Cys Phe Arg
    355                 360                 365

Leu Arg Lys Lys Asn Gln Met Ser Lys Leu Ile Ser Glu Met His Ser
370                 375                 380

Phe Ile Gln Ile Lys Lys Lys Thr Asn Pro Arg Asn Asn Asp Pro Lys
385                 390                 395                 400

Ser Met Lys Leu Pro Gln Glu Gln Arg Gln Leu Pro Tyr Pro Ser Glu
            405                 410                 415

Ala Ser Thr Thr Phe Pro Glu Ser His Leu Arg Thr Pro Gln Met Pro
        420                 425                 430

Pro Thr Thr Pro Ser Ser Ser Phe Phe Thr Lys Lys Ser Glu Asp Thr
    435                 440                 445

Ile Ser Lys Met Asn Asp Phe Met Arg Met Gln Ile Leu Lys Glu Gly
450                 455                 460

Ser His Phe Pro Gly Pro Phe Met Thr Ser Ile Gly Pro Ala Glu Ser
465                 470                 475                 480

His Pro His Thr Pro Gln Met Pro Pro Ser Thr Pro Ser Ser Ser Phe
            485                 490                 495

Leu Thr Thr Lys Ser Glu Asp Thr Ile Ser Lys Met Asn Asp Phe Met
        500                 505                 510

Arg Met Gln Ile Leu Lys Glu Gly Ser His Phe Pro Gly Pro Phe Met
    515                 520                 525

Thr Ser Ile Gly Pro Ala Glu Ser His Pro His Thr Pro Gln Met Pro
530                 535                 540

Pro Ser Thr Pro Ser Ser Ser Phe Leu Thr Thr Leu Lys Pro Arg Leu
545                 550                 555                 560

Lys Thr Glu Pro Glu Glu Val Ser Ile Glu Asp Ser Ala Gln Ser Asp
            565                 570                 575

Leu Lys Glu Val Met Val Leu Asn Ala Thr Glu Ser Phe Val Tyr Glu
        580                 585                 590

Pro Lys Glu Gln Lys Lys Met Phe His Ala Thr Val Ala Thr Glu Asn
    595                 600                 605

Glu Val Phe Arg Val Lys Val Phe Asn Ile Asp Leu Lys Glu Lys Phe
610                 615                 620

Thr Pro Lys Lys Ile Ile Ala Ile Ala Asn Tyr Val Cys Arg Asn Gly
625                 630                 635                 640

Phe Leu Glu Val Tyr Pro Phe Thr Leu Val Ala Asp Val Asn Ala Asp
            645                 650                 655

Arg Asn Met Glu Ile Pro Lys Gly Leu Ile Arg Ser Ala Ser Val Thr
        660                 665                 670

Pro Lys Ile Asn Gln Leu Cys Ser Gln Thr Lys Gly Ser Phe Val Asn
    675                 680                 685

Gly Val Phe Glu Val His Lys Lys Asn Val Arg Gly Glu Phe Thr Tyr
690                 695                 700

Tyr Glu Ile Gln Asp Asn Thr Gly Lys Met Glu Val Val Val His Gly
705                 710                 715                 720
```

```
Arg Leu Thr Thr Ile Asn Cys Glu Glu Gly Asp Lys Leu Lys Leu Thr
                725                 730                 735

Cys Phe Glu Leu Ala Pro Lys Ser Gly Asn Thr Gly Glu Leu Arg Ser
            740                 745                 750

Val Ile His Ser His Ile Lys Val Ile Lys Thr Arg Lys Asn Lys Lys
        755                 760                 765

Asp Ile Leu Asn Pro Asp Ser Ser Met Glu Thr Ser Pro Asp Phe Phe
    770                 775                 780

Phe
785

<210> SEQ ID NO 3
<211> LENGTH: 729
<212> TYPE: PRT
<213> ORGANISM: Homo sapiens

<400> SEQUENCE: 3

Met Gly Lys Lys Tyr Lys Asn Ile Val Leu Leu Lys Gly Leu Glu Val
1               5                   10                  15

Ile Asn Asp Tyr His Phe Arg Met Val Lys Ser Leu Leu Ser Asn Asp
            20                  25                  30

Leu Lys Leu Asn Leu Lys Met Arg Glu Glu Tyr Asp Lys Ile Gln Ile
        35                  40                  45

Ala Asp Leu Met Glu Glu Lys Phe Arg Gly Asp Ala Gly Leu Gly Lys
    50                  55                  60

Leu Ile Lys Ile Phe Glu Asp Ile Pro Thr Leu Glu Asp Leu Ala Glu
65                  70                  75                  80

Thr Leu Lys Lys Glu Lys Leu Lys Val Lys Gly Pro Ala Leu Ser Arg
                85                  90                  95

Lys Arg Lys Lys Glu Val Asp Ala Thr Ser Pro Ala Pro Ser Thr Ser
            100                 105                 110

Ser Thr Val Lys Thr Glu Gly Ala Glu Ala Thr Pro Gly Ala Gln Lys
        115                 120                 125

Arg Lys Lys Ser Thr Lys Glu Lys Ala Gly Pro Lys Gly Ser Lys Val
    130                 135                 140

Ser Glu Glu Gln Thr Gln Pro Pro Ser Pro Ala Gly Ala Gly Met Ser
145                 150                 155                 160

Thr Ala Met Gly Arg Ser Pro Ser Pro Lys Thr Ser Leu Ser Ala Pro
                165                 170                 175

Pro Asn Ser Ser Ser Thr Glu Asn Pro Lys Thr Val Ala Lys Cys Gln
            180                 185                 190

Val Thr Pro Arg Arg Asn Val Leu Gln Lys Arg Pro Val Ile Val Lys
        195                 200                 205

Val Leu Ser Thr Thr Lys Pro Phe Glu Tyr Glu Thr Pro Glu Met Glu
    210                 215                 220

Lys Lys Ile Met Phe His Ala Thr Val Ala Thr Gln Thr Gln Phe Phe
225                 230                 235                 240

His Val Lys Val Leu Asn Thr Ser Leu Lys Glu Lys Phe Asn Gly Lys
                245                 250                 255

Lys Ile Ile Ile Ser Asp Tyr Leu Glu Tyr Asp Ser Leu Leu Glu
            260                 265                 270

Val Asn Glu Glu Ser Thr Val Ser Glu Ala Gly Pro Asn Gln Thr Phe
        275                 280                 285

Glu Val Pro Asn Lys Ile Ile Asn Arg Ala Lys Glu Thr Leu Lys Ile
    290                 295                 300
```

```
Asp Ile Leu His Lys Gln Ala Ser Gly Asn Ile Val Tyr Gly Val Phe
305                 310                 315                 320

Met Leu His Lys Lys Thr Val Asn Gln Lys Thr Thr Ile Tyr Glu Ile
            325                 330                 335

Gln Asp Asp Arg Gly Lys Met Asp Val Val Gly Thr Gly Gln Cys His
                340                 345                 350

Asn Ile Pro Cys Glu Glu Gly Asp Lys Leu Gln Leu Phe Cys Phe Arg
            355                 360                 365

Leu Arg Lys Lys Asn Gln Met Ser Lys Leu Ile Ser Glu Met His Ser
        370                 375                 380

Phe Ile Gln Ile Lys Lys Thr Asn Pro Arg Asn Asn Asp Pro Lys
385                 390                 395                 400

Ser Met Lys Leu Pro Gln Glu Gln Arg Gln Leu Pro Tyr Pro Ser Glu
                405                 410                 415

Ala Ser Thr Thr Phe Pro Glu Ser His Leu Arg Thr Pro Gln Met Pro
                420                 425                 430

Pro Thr Thr Pro Ser Ser Ser Phe Phe Thr Lys Lys Ser Glu Asp Thr
            435                 440                 445

Ile Ser Lys Met Asn Asp Phe Met Arg Met Gln Ile Leu Lys Glu Gly
        450                 455                 460

Ser His Phe Pro Gly Pro Phe Met Thr Ser Ile Gly Pro Ala Glu Ser
465                 470                 475                 480

His Pro His Thr Pro Gln Met Pro Pro Ser Thr Pro Ser Ser Ser Phe
                485                 490                 495

Leu Thr Thr Leu Lys Pro Arg Leu Lys Thr Glu Pro Glu Glu Val Ser
                500                 505                 510

Ile Glu Asp Ser Ala Gln Ser Asp Leu Lys Glu Val Met Val Leu Asn
            515                 520                 525

Ala Thr Glu Ser Phe Val Tyr Glu Pro Lys Glu Gln Lys Lys Met Phe
        530                 535                 540

His Ala Thr Val Ala Thr Glu Asn Glu Val Phe Arg Val Lys Val Phe
545                 550                 555                 560

Asn Ile Asp Leu Lys Glu Lys Phe Thr Pro Lys Lys Ile Ile Ala Ile
                565                 570                 575

Ala Asn Tyr Val Cys Arg Asn Gly Phe Leu Glu Val Tyr Pro Phe Thr
            580                 585                 590

Leu Val Ala Asp Val Asn Ala Asp Arg Asn Met Glu Ile Pro Lys Gly
        595                 600                 605

Leu Ile Arg Ser Ala Ser Val Thr Pro Lys Ile Asn Gln Leu Cys Ser
        610                 615                 620

Gln Thr Lys Gly Ser Phe Val Asn Gly Val Phe Glu Val His Lys Lys
625                 630                 635                 640

Asn Val Arg Gly Glu Phe Thr Tyr Tyr Glu Ile Gln Asp Asn Thr Gly
                645                 650                 655

Lys Met Glu Val Val Val His Gly Arg Leu Thr Thr Ile Asn Cys Glu
            660                 665                 670

Glu Gly Asp Lys Leu Lys Leu Thr Cys Phe Glu Leu Ala Pro Lys Ser
        675                 680                 685

Gly Asn Thr Gly Glu Leu Arg Ser Val Ile His Ser His Ile Lys Val
        690                 695                 700
```

Ile Lys Thr Arg Lys Asn Lys Lys Asp Ile Leu Asn Pro Asp Ser Ser
705                 710                 715                 720

Met Glu Thr Ser Pro Asp Phe Phe
                725

<210> SEQ ID NO 4
<211> LENGTH: 673
<212> TYPE: PRT
<213> ORGANISM: Homo sapiens

<400> SEQUENCE: 4

Met Gly Lys Lys Tyr Lys Asn Ile Val Leu Leu Lys Gly Leu Glu Val
1               5                   10                  15

Ile Asn Asp Tyr His Phe Arg Met Val Lys Ser Leu Leu Ser Asn Asp
                20                  25                  30

Leu Lys Leu Asn Leu Lys Met Arg Glu Glu Tyr Asp Lys Ile Gln Ile
            35                  40                  45

Ala Asp Leu Met Glu Glu Lys Phe Arg Gly Asp Ala Gly Leu Gly Lys
50                  55                  60

Leu Ile Lys Ile Phe Glu Asp Ile Pro Thr Leu Glu Asp Leu Ala Glu
65                  70                  75                  80

Thr Leu Lys Lys Glu Lys Leu Lys Val Lys Gly Pro Ala Leu Ser Arg
                85                  90                  95

Lys Arg Lys Lys Glu Val Asp Ala Thr Ser Pro Ala Pro Ser Thr Ser
            100                 105                 110

Ser Thr Val Lys Thr Glu Gly Ala Glu Ala Thr Pro Gly Ala Gln Lys
        115                 120                 125

Arg Lys Lys Ser Thr Lys Glu Lys Ala Gly Pro Lys Gly Ser Lys Val
    130                 135                 140

Ser Glu Glu Gln Thr Gln Pro Pro Ser Pro Ala Gly Ala Gly Met Ser
145                 150                 155                 160

Thr Ala Met Gly Arg Ser Pro Ser Pro Lys Thr Ser Leu Ser Ala Pro
                165                 170                 175

Pro Asn Ser Ser Ser Thr Glu Asn Pro Lys Thr Val Ala Lys Cys Gln
            180                 185                 190

Val Thr Pro Arg Arg Asn Val Leu Gln Lys Arg Pro Val Ile Val Lys
        195                 200                 205

Val Leu Ser Thr Thr Lys Pro Phe Glu Tyr Glu Thr Pro Glu Met Glu
    210                 215                 220

Lys Lys Ile Met Phe His Ala Thr Val Ala Thr Gln Thr Gln Phe Phe
225                 230                 235                 240

His Val Lys Val Leu Asn Thr Ser Leu Lys Glu Lys Phe Asn Gly Lys
                245                 250                 255

Lys Ile Ile Ile Ile Ser Asp Tyr Leu Glu Tyr Asp Ser Leu Leu Glu
            260                 265                 270

Val Asn Glu Glu Ser Thr Val Ser Glu Ala Gly Pro Asn Gln Thr Phe
        275                 280                 285

Glu Val Pro Asn Lys Ile Ile Asn Arg Ala Lys Glu Thr Leu Lys Ile
    290                 295                 300

Asp Ile Leu His Lys Gln Ala Ser Gly Asn Ile Val Tyr Gly Val Phe
305                 310                 315                 320

Met Leu His Lys Lys Thr Val Asn Gln Lys Thr Thr Ile Tyr Glu Ile
                325                 330                 335

Gln Asp Asp Arg Gly Lys Met Asp Val Val Gly Thr Gly Gln Cys His
            340                 345                 350

```
Asn Ile Pro Cys Glu Glu Gly Asp Lys Leu Gln Leu Phe Cys Phe Arg
            355                 360                 365
Leu Arg Lys Lys Asn Gln Met Ser Lys Leu Ile Ser Glu Met His Ser
    370                 375                 380
Phe Ile Gln Ile Lys Lys Thr Asn Pro Arg Asn Asn Asp Pro Lys
385                 390                 395                 400
Ser Met Lys Leu Pro Gln Glu Gln Arg Gln Leu Pro Tyr Pro Ser Glu
                405                 410                 415
Ala Ser Thr Thr Phe Pro Glu Ser His Leu Arg Thr Pro Gln Met Pro
            420                 425                 430
Pro Thr Thr Pro Ser Ser Ser Phe Phe Thr Lys Leu Lys Pro Arg Leu
    435                 440                 445
Lys Thr Glu Pro Glu Glu Val Ser Ile Glu Asp Ser Ala Gln Ser Asp
450                 455                 460
Leu Lys Glu Val Met Val Leu Asn Ala Thr Glu Ser Phe Val Tyr Glu
465                 470                 475                 480
Pro Lys Glu Gln Lys Met Phe His Ala Thr Val Ala Thr Glu Asn
                485                 490                 495
Glu Val Phe Arg Val Lys Val Phe Asn Ile Asp Leu Lys Glu Lys Phe
            500                 505                 510
Thr Pro Lys Lys Ile Ala Ile Ala Asn Tyr Val Cys Arg Asn Gly
    515                 520                 525
Phe Leu Glu Val Tyr Pro Phe Thr Leu Val Ala Asp Val Asn Ala Asp
    530                 535                 540
Arg Asn Met Glu Ile Pro Lys Gly Leu Ile Arg Ser Ala Ser Val Thr
545                 550                 555                 560
Pro Lys Ile Asn Gln Leu Cys Ser Gln Thr Lys Gly Ser Phe Val Asn
                565                 570                 575
Gly Val Phe Glu Val His Lys Lys Asn Val Arg Gly Glu Phe Thr Tyr
            580                 585                 590
Tyr Glu Ile Gln Asp Asn Thr Gly Lys Met Glu Val Val Val His Gly
    595                 600                 605
Arg Leu Thr Thr Ile Asn Cys Glu Glu Gly Asp Lys Leu Lys Leu Thr
    610                 615                 620
Cys Phe Glu Leu Ala Pro Lys Ser Gly Asn Thr Gly Glu Leu Arg Ser
625                 630                 635                 640
Val Ile His Ser His Ile Lys Val Ile Lys Thr Arg Lys Asn Lys Lys
                645                 650                 655
Asp Ile Leu Asn Pro Asp Ser Ser Met Glu Thr Ser Pro Asp Phe Phe
            660                 665                 670
Phe

<210> SEQ ID NO 5
<211> LENGTH: 2709
<212> TYPE: DNA
<213> ORGANISM: Homo sapiens

<400> SEQUENCE: 5
gggaatagca gaataggagc aagccagcac tagtcagcta actaagtgac tcaaccaagg      60
ccttttttcc ttgttatctt tgcagatact tcatttctct agcgtttctg gagattacaa     120
catcctgcgg ttccgtttct gggaacttta ctgatttatc tccccctca cacaaataag      180 cattgattcc tgcatttctg aagatctcaa gatctggact actgttgaaa aaatttccag     240
tgaggctcac ttatgtctgt aaagatggga aaaaaataca gaacattgt tctactaaaa      300
```

```
ggattagagg tcatcaatga ttatcatttt agaatggtta agtccttact gagcaacgat    360
ttaaaactta atttaaaaat gagagaagag tatgacaaaa ttcagattgc tgacttgatg    420
gaagaaaagt tccgaggtga tgctggtttg ggcaaactaa taaaaatttt cgaagatata    480
ccaacgcttg aagacctggc tgaaactctt aaaaagaaa agttaaaagt aaaaggacca    540
gccctatcaa gaaagaggaa gaaggaagtg catgctactt cacctgcacc ctccacaagc    600
agcactgtca aaactgaagg agcagaggca actcctggag ctcagaaaag aaaaaaatca    660
accaaagaaa aggctggacc caagggagt aaggtgtccg aggaacagac tcagcctccc     720
tctcctgcag gagccggcat gtccacagcc atgggccgtt ccccatctcc caagacctca    780
ttgtcagctc cacccaacag ttcttcaact gagaacccga aaacagtggc caaatgtcag    840
gtaactccca gaagaaatgt tctccaaaaa cgcccagtga tagtgaaggt actgagtaca    900
acaaagccat ttgaatatga gaccccagaa atggagaaaa aataatgtt tcatgctaca    960 gtggctacac agacacagtt cttccatgtg aaggtttaa acaccagctt gaaggagaaa    1020
ttcaatggaa agaaaatcat catcatatca gattatttgg aatatgatag tctcctagag    1080
gtcaatgaag aatctactgt atctgaagct ggtcctaacc aaacgtttga ggttccaaat     1140
aaaatcatca acagagcaaa ggaaactctg aagattgata ttcttcacaa acaagcttca    1200
ggaaatattg tatatggggt atttatgcta cataagaaaa cagtaaatca gaagaccaca    1260
atctacgaaa ttcaggatga tagaggaaaa atggatgtag tggggacagg acaatgtcac    1320
aatatcccct gtgaagaagg agataagctc cagcttttct gctttcgact tagaaaaaag    1380
aaccagatgt caaaactgat ttcagaaatg catagtttta tccagataaa gaaaaaaaca    1440
aacccgagaa acaatgaccc caagagcatg aagctacccc aggaacagcg tcagcttcca    1500
tatccttcag aggccagcac aaccttccct gagagccatc ttcggactcc tcagatgcca    1560
ccaacaactc catccagcag tttcttcacc aagaaaagtg aagacacaat ctccaaaatg    1620
aatgacttca tgaggatgca gatactgaag gaagggagtc attttccagg accgttcatg    1680
accagcatag gcccagctga gagccatccc cacactcctc agatgcctcc atcaacacca    1740
agcagcagtt tcttaaccac gttgaaacca agactgaaga ctgaacctga gaagtttcc    1800 atagaagaca gtgcccagag tgacctcaaa gaagtgatgg tgctgaacgc aacagaatca    1860
tttgtatatg agcccaaaga gcagaagaaa atgtttcatg ccacagtggc aactgagaat    1920
gaagtcttcc gagtgaaggt ttttaatatt gacctaaagg agaagttcac cccaaagaag    1980
atcattgcca tagcaaatta tgtttgccgc aatgggttcc tggaggtata tcctttcaca    2040
cttgtggctg atgtgaatgc tgaccgaaac atggagatcc aaaaggatt gattagaagt    2100 gccagcgtaa ctcctaaaat caatcagctt tgctcacaaa ctaaaggaag ttttgtgaat    2160
ggggtgtttg aggtacataa gaaaaatgta aggggtgaat tcacttatta tgaaatacaa    2220
gataatacag gaagatgga agtggtggtg catggacgac tgaacacaat caactgtgag    2280
gaaggagata aactgaaact caccagcttt gaattggcac cgaaaagtgg gaataccggg    2340
gagttgagat ctgtaattca tagtcacatc aaggtcatca agaccaggaa aaacaagaaa    2400
gacatactca atcctgattc aagtatggaa acttcaccag acttttcctt ctaaaatctg    2460
gatgtcattg acgataatgt ttatggagat aaggtctaag tccctaaaaa aatgtacata    2520
tacctggttg aaatacaaca ctatacatac acaccaccat atatactagc tgttaatcct    2580
atggaatggg ggtattggga gtgcttttt aatttttcat agttttttttt taataaaatg    2640
```

```
gcatattttg catctacaac ttctataata agaaaaaata aataaacatt atctttttg   2700 tgaaaaaaa                                                          2709
```

<210> SEQ ID NO 6
<211> LENGTH: 19
<212> TYPE: RNA
<213> ORGANISM: Artificial Sequence
<220> FEATURE:
<223> OTHER INFORMATION: Chemically synthesized

<400> SEQUENCE: 6

```
gaucuguaau ucauaguca                                               19
```

<210> SEQ ID NO 7
<211> LENGTH: 19
<212> TYPE: RNA
<213> ORGANISM: Artificial Sequence
<220> FEATURE:
<223> OTHER INFORMATION: Chemically synthesized

<400> SEQUENCE: 7

```
ggaccagccc uaucaagaa                                               19
```

<210> SEQ ID NO 8
<211> LENGTH: 19
<212> TYPE: RNA
<213> ORGANISM: Artificial Sequence
<220> FEATURE:
<223> OTHER INFORMATION: Chemically synthesized

<400> SEQUENCE: 8

```
ggaguaaggu guccgagga                                               19
```

<210> SEQ ID NO 9
<211> LENGTH: 19
<212> TYPE: RNA
<213> ORGANISM: Artificial Sequence
<220> FEATURE:
<223> OTHER INFORMATION: Chemically synthesized

<400> SEQUENCE: 9

```
cagcguaacu ccuaaaauc                                               19
```

<210> SEQ ID NO 10
<211> LENGTH: 19
<212> TYPE: RNA
<213> ORGANISM: Artificial Sequence
<220> FEATURE:
<223> OTHER INFORMATION: Chemically synthesized

<400> SEQUENCE: 10

```
gcugguccua accaaacgu                                               19
```

<210> SEQ ID NO 11
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 11

```
ccacaaucua cgaaauuca                                               19
```

```
<210> SEQ ID NO 12
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 12
ugaauuucgu agauugugg                                                  19

<210> SEQ ID NO 13
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 13
ccauccagca guucuuca                                                   19

<210> SEQ ID NO 14
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 14
ugaagaaacu gcuggaugg                                                  19

<210> SEQ ID NO 15
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 15
ggaaggagau aaacugaaa                                                  19

<210> SEQ ID NO 16
<211> LENGTH: 19
<212> TYPE: RNA
<213> ORGANISM: Artificial Sequence
<220> FEATURE:
<223> OTHER INFORMATION: Chemcially synthesized

<400> SEQUENCE: 16
uuucaguuua ucuccuucc                                                  19

<210> SEQ ID NO 17
<211> LENGTH: 619
<212> TYPE: PRT
<213> ORGANISM: Mus musculus

<400> SEQUENCE: 17

Met Val Asn Glu Tyr Lys Arg Ile Val Leu Leu Arg Gly Leu Glu Cys
1               5                   10                  15

Ile Asn Lys His Tyr Phe Ser Leu Phe Lys Ser Leu Leu Ala Arg Asp
                20                  25                  30

Leu Asn Leu Glu Arg Asp Asn Gln Glu Gln Tyr Thr Thr Ile Gln Ile
            35                  40                  45

Ala Asn Met Met Glu Glu Lys Phe Pro Ala Asp Ser Gly Leu Gly Lys
        50                  55                  60
```

-continued

```
Leu Ile Ala Phe Cys Glu Glu Val Pro Ala Leu Arg Lys Arg Ala Glu
 65                  70                  75                  80

Ile Leu Lys Lys Glu Arg Ser Glu Val Thr Gly Glu Thr Ser Leu Glu
                 85                  90                  95

Lys Asn Gly Gln Glu Ala Gly Pro Ala Thr Pro Thr Ser Thr Thr Ser
            100                 105                 110

His Met Leu Ala Ser Glu Arg Gly Glu Thr Ser Ala Thr Gln Glu Glu
        115                 120                 125

Thr Ser Thr Ala Gln Ala Gly Thr Ser Thr Ala Gln Ala Arg Thr Ser
    130                 135                 140

Thr Ala Gln Ala Gly Thr Ser Thr Ala Gln Lys Arg Lys Ile Met Arg
145                 150                 155                 160

Glu Glu Glu Thr Gly Val Lys Lys Ser Lys Ala Ala Lys Glu Pro Asp
                165                 170                 175

Gln Pro Pro Cys Cys Glu Glu Pro Thr Ala Arg Cys Gln Ser Pro Ile
            180                 185                 190

Leu His Ser Ser Ser Ala Ser Ser Asn Ile Pro Ser Ala Lys Asn
        195                 200                 205

Gln Lys Ser Gln Pro Gln Asn Gln Asn Ile Pro Arg Gly Ala Val Leu
    210                 215                 220

His Ser Glu Pro Leu Thr Val Met Val Leu Thr Ala Thr Asp Pro Phe
225                 230                 235                 240

Glu Tyr Glu Ser Pro Glu His Glu Val Lys Asn Met Leu His Ala Thr
                245                 250                 255

Val Ala Thr Val Ser Gln Tyr Phe His Val Lys Val Phe Asn Ile Asn
            260                 265                 270

Leu Lys Glu Lys Phe Thr Lys Asn Phe Ile Ile Ile Ser Asn Tyr
        275                 280                 285

Phe Glu Ser Lys Gly Ile Leu Glu Ile Asn Glu Thr Ser Ser Val Leu
    290                 295                 300

Glu Ala Ala Pro Asp Gln Met Ile Glu Val Pro Asn Ser Ile Ile Arg
305                 310                 315                 320

Asn Ala Asn Ala Ser Pro Lys Ile Cys Asp Ile Gln Lys Gly Thr Ser
                325                 330                 335

Gly Ala Val Phe Tyr Gly Val Phe Thr Leu His Lys Lys Thr Val Asn
            340                 345                 350

Arg Lys Asn Thr Ile Tyr Glu Ile Lys Asp Gly Ser Gly Ser Ile Glu
        355                 360                 365

Val Val Gly Ser Gly Lys Trp His Asn Ile Asn Cys Lys Glu Gly Asp
    370                 375                 380

Lys Leu His Leu Phe Cys Phe His Leu Lys Thr Ile Asp Arg Gln Pro
385                 390                 395                 400

Lys Leu Val Cys Gly Glu His Ser Phe Ile Lys Ile Ser Lys Arg Gly
                405                 410                 415

Asn Val Pro Lys Glu Pro Ala Lys Glu Glu Asp His His Gly Pro
            420                 425                 430

Lys Gln Val Met Val Leu Lys Val Thr Glu Pro Phe Thr Tyr Asp Leu
        435                 440                 445

Lys Glu Asp Lys Arg Met Phe His Ala Thr Val Ala Thr Glu Thr Glu
    450                 455                 460

Phe Phe Arg Val Lys Val Phe Asp Thr Ala Leu Lys Ser Lys Phe Ile
465                 470                 475                 480
```

```
Pro Arg Asn Ile Ile Ala Ile Ser Asp Tyr Phe Gly Cys Asn Gly Phe
                485                 490                 495

Leu Glu Ile Tyr Arg Ala Ser Cys Val Ser Asp Val Asn Val Asn Pro
        500                 505                 510

Thr Met Val Ile Ser Asn Thr Leu Arg Gln Arg Ala Asn Ala Thr Pro
        515                 520                 525

Lys Ile Ser Tyr Leu Phe Ser Gln Ala Arg Gly Thr Phe Val Ser Gly
        530                 535                 540

Glu Tyr Leu Val Asn Lys Lys Thr Glu Arg Asn Lys Phe Ile Tyr Tyr
545                 550                 555                 560

Gly Ile Gly Asp Asp Thr Gly Lys Met Glu Val Val Tyr Gly Arg
                565                 570                 575

Leu Thr Asn Val Arg Cys Glu Pro Gly Ser Lys Leu Arg Leu Val Cys
                580                 585                 590

Phe Glu Leu Thr Ser Thr Glu Asp Gly Trp Gln Leu Arg Ser Val Arg
                595                 600                 605

His Ser Tyr Met Gln Val Ile Asn Ala Arg Lys
        610                 615

<210> SEQ ID NO 18
<211> LENGTH: 2302
<212> TYPE: DNA
<213> ORGANISM: Mus musculus

<400> SEQUENCE: 18
agtttcttat ttactgactt agctgcctac ctactcaagc caagcaggcc acttcttgac      60
ccggtgaagg tctcaggatc tgtacatcac tgcagaaata tccaggaagg ctcagcaaca     120
acttcaaaga tggtgaatga atacaagaga attgttctgc tgagaggact tgaatgtatc     180
aataagcatt attttagctt atttaagtca ttgctggcca gagatttaaa tctggaaaga     240
gacaaccaag agcaatacac cacgattcag attgctaaca tgatggaaga gaaatttcca     300
gctgattctg gattgggcaa actgattgcg ttttgtgaag aagtaccagc tcttagaaaa     360
cgagctgaaa ttcttaaaaa agagagatca gaagtaacag gagaaacatc actggaaaaa     420
aatggtcaag aagcaggtcc tgcaacacct acatcaacta caagccacat gttagcatct     480
gaaagaggcg agacttctgc aacccaggaa gagacttcca cagctcaggc ggggacttcc     540
acagctcagg cgaggacttc cacagctcag gcggggactt ctacagccca gaaaagaaaa     600
attatgagag aagaagagac tggagtgaaa aagagcaagg cggctaagga accagatcag     660
cctccctgtt gtgaagaacc cacagccagg tgccagtcac caatactcca cagctcatct     720
tcagcttcat ctaacattcc ttcggctaag aaccaaaaat cacaacccca gaatcagaac     780
attcccagag gtgctgttct ccactcagag cccctgacag tgatggtgct cactgcaaca     840
gacccatttg aatatgaatc accagaacat gaagtaaaga acatgcttca tgctacagtg     900
gctacagtga gccagtattt ccatgtgaaa gttttcaaca tcaacttgaa agaaaagttc     960
acaaaaaaga atttttatcat catatccaat tactttgaga gcaaaggcat cctggagatc    1020
aatgagactt cctctgtgtt agaggctgct cctgaccaaa tgattgaagt gcccaacagt    1080
attatcagaa atgcaaatgc cagccctaag atctgtgata ttcaaaaggg tacttctgga    1140
gcagtgttct atggagtgtt tacattcacc aagaaaacag tgaaccgaaa gaacacaatc    1200
tatgaaataa aagatggttc aggaagcata gaagtggtgg ggagtggaaa atggcacaac    1260
atcaactgca aggaaggaga taaactccac ctcttctgct ttcacctgaa aacaattgac    1320
```

-continued

```
aggcaaccaa agttagtgtg tggagaacac agtttcatca agatatcaaa gagaggaaat    1380
gtaccaaagg agcctgctaa ggaagaagat caccatcatg gtcccaaaca agtgatggtg    1440
ctgaaagtaa cagaaccatt tacatatgac ctgaaagagg ataaaagaat gtttcatgct    1500
accgtggcta ctgaaactga gttcttcaga gtgaaggttt ttgacacggc tctaaagagc    1560
aagttcatcc caagaaatat cattgccata tcagattatt ttgggtgcaa tgggtttctg    1620
gagatataca gagcttcctg tgtctctgat gtgaacgtta atccaacaat ggttatctca    1680
aatacactga gacaaagagc taatgcaact cctaaaattt cttatctttt ctcacaagca    1740
agggggacat ttgtgagtgg agagtactta gtaaataaga aaacggagag gaataaattc    1800
atttactatg gaattggaga tgatacaggg aaaatggaag tggtggttta tggaagactc    1860
accaatgtca ggtgtgaacc aggcagtaaa ctaagacttg tctgctttga attgacttcc    1920
actgaagatg ggtggcagct gaggtctgta aggcacagtt acatgcaggt catcaatgct    1980
agaaagtgaa ggaaagccac tcaacccaga ctcagtcggg agaacctctc tggaaccata    2040
cttctgaaaa cctgaatgcc aatgatattt ttttgtggag ataagattca attacagaaa    2100
ataaatgtgt ataagcctat tgaaatatca gtcctataaa gaccatctct taattctagg    2160
aaatggtgtt ttcttatatt ctttacacat tttctatatc taaattcatt tgttgtctct    2220
ataacttcta taactgttca atttgcaatt tttatgccta aaacttataa aaataaattc    2280
acacaatttc tgtaaaaaaa aa                                              2302
```

<210> SEQ ID NO 19
<211> LENGTH: 19
<212> TYPE: RNA
<213> ORGANISM: Artificial Sequence
<220> FEATURE:
<223> OTHER INFORMATION: Chemically synthesized

<400> SEQUENCE: 19
gaucuguaau ucauaguca                                                   19

<210> SEQ ID NO 20
<211> LENGTH: 19
<212> TYPE: RNA
<213> ORGANISM: Artificial Sequence
<220> FEATURE:
<223> OTHER INFORMATION: Chemically synthesized

<400> SEQUENCE: 20
ggaccagccc uaucaagaa                                                   19

<210> SEQ ID NO 21
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 21
ggaguaaggu guccgagga                                                   19

<210> SEQ ID NO 22
<211> LENGTH: 19
<212> TYPE: RNA
<213> ORGANISM: Artificial Sequence
<220> FEATURE:
<223> OTHER INFORMATION: Chemically synthesized

```
<400> SEQUENCE: 22
cagcguaacu ccuaaaauc                                                    19

<210> SEQ ID NO 23
<211> LENGTH: 19
<212> TYPE: RNA
<213> ORGANISM: Artificial Sequence
<220> FEATURE:
<223> OTHER INFORMATION: Chemcially synthesized

<400> SEQUENCE: 23
gcugguccua accaaacgu                                                    19

<210> SEQ ID NO 24
<211> LENGTH: 20
<212> TYPE: DNA
<213> ORGANISM: Artificial Sequence
<220> FEATURE:
<223> OTHER INFORMATION: Chemically synthesized

<400> SEQUENCE: 24
aaactcatga gcagtctgca                                                   20

<210> SEQ ID NO 25
<211> LENGTH: 22
<212> TYPE: DNA
<213> ORGANISM: Artificial Sequence
<220> FEATURE:
<223> OTHER INFORMATION: chemically synthesized

<400> SEQUENCE: 25
aggagatctt cagtttcgga gg                                                22

<210> SEQ ID NO 26
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 26
gcattcgtat tgcgccgcta                                                   20

<210> SEQ ID NO 27
<211> LENGTH: 15
<212> TYPE: DNA
<213> ORGANISM: Artificial Sequence
<220> FEATURE:
<223> OTHER INFORMATION: Chemically synthesized

<400> SEQUENCE: 27
agctgcccgg cgggt                                                        15

<210> SEQ ID NO 28
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 28
actgagtaca acaaagccat ttga                                              24
```

```
<210> SEQ ID NO 29
<211> LENGTH: 23
<212> TYPE: DNA
<213> ORGANISM: Artificial Sequence
<220> FEATURE:
<223> OTHER INFORMATION: Chemically synthesized

<400> SEQUENCE: 29
ttgtgacatt gtcctgtccc cac                                              23

<210> SEQ ID NO 30
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 30
cctgagcaga acaactgc                                                    18

<210> SEQ ID NO 31
<211> LENGTH: 21
<212> TYPE: DNA
<213> ORGANISM: Artificial Sequence
<220> FEATURE:
<223> OTHER INFORMATION: Chemically synthesized

<400> SEQUENCE: 31
ggtcttcaag ctgcccacag t                                                21

<210> SEQ ID NO 32
<211> LENGTH: 200
<212> TYPE: PRT
<213> ORGANISM: Homo sapiens

<400> SEQUENCE: 32
```

Gln Glu Ser Ile Arg Glu Gly Phe Gln Lys Arg Cys Leu Pro Val Met
1               5                   10                  15

Val Leu Lys Ala Lys Lys Pro Phe Thr Phe Glu Thr Gln Glu Gly Lys
            20                  25                  30

Gln Glu Met Phe His Ala Thr Val Ala Thr Glu Lys Glu Phe Phe Phe
        35                  40                  45

Val Lys Val Phe Asn Thr Leu Leu Lys Asp Lys Phe Ile Pro Lys Arg
    50                  55                  60

Ile Ile Ile Ile Ala Arg Tyr Tyr Arg His Ser Gly Phe Leu Glu Val
65                  70                  75                  80

Asn Ser Ala Ser Arg Val Leu Asp Ala Glu Ser Asp Gln Lys Val Asn
                85                  90                  95

Val Pro Leu Asn Ile Ile Arg Lys Ala Gly Glu Thr Pro Lys Ile Asn
            100                 105                 110

Thr Leu Gln Thr Gln Pro Leu Gly Thr Ile Val Asn Gly Leu Phe Val
        115                 120                 125

Val Gln Lys Val Thr Glu Lys Lys Asn Ile Leu Phe Asp Leu Ser
    130                 135                 140

Asp Asn Thr Gly Lys Met Glu Val Leu Gly Val Arg Asn Glu Asp Thr
145                 150                 155                 160

Met Lys Cys Lys Glu Gly Asp Lys Val Arg Leu Thr Phe Phe Thr Leu
                165                 170                 175

```
Ser Lys Asn Gly Glu Lys Leu Gln Leu Thr Ser Gly Val His Ser Thr
            180                 185                 190

Ile Lys Val Ile Lys Ala Lys Lys
        195                 200

<210> SEQ ID NO 33
<211> LENGTH: 198
<212> TYPE: PRT
<213> ORGANISM: Mus musculus

<400> SEQUENCE: 33

Gln Glu Ala Ile Arg Glu Asp Leu Gln Lys Asp Pro Leu Val Val Thr
1               5                   10                  15

Val Leu Lys Ala Ile Asn Pro Phe Glu Cys Glu Thr Gln Glu Gly Arg
            20                  25                  30

Gln Glu Ile Phe His Ala Thr Val Ala Thr Glu Thr Asp Phe Phe Phe
        35                  40                  45

Val Lys Val Leu Asn Ala Gln Phe Lys Asp Lys Phe Ile Pro Lys Arg
50                  55                  60

Thr Ile Lys Ile Ser Asn Tyr Leu Trp His Ser Asn Phe Met Glu Val
65                  70                  75                  80

Thr Ser Ser Ser Val Val Asp Val Glu Ser Asn His Glu Val Pro
                85                  90                  95

Asn Asn Val Val Lys Arg Ala Arg Glu Thr Pro Arg Ile Ser Lys Leu
            100                 105                 110

Lys Ile Gln Pro Cys Gly Thr Ile Val Asn Gly Leu Phe Lys Val Gln
        115                 120                 125

Lys Ile Thr Glu Glu Lys Asp Arg Val Leu Tyr Gly Ile His Asp Lys
130                 135                 140

Thr Gly Thr Met Glu Val Leu Val Leu Gly Asn Pro Ser Lys Thr Lys
145                 150                 155                 160

Cys Glu Glu Gly Asp Lys Ile Arg Leu Thr Phe Phe Glu Val Ser Lys
                165                 170                 175

Asn Gly Val Lys Ile Gln Leu Lys Ser Gly Pro Cys Ser Phe Phe Lys
            180                 185                 190

Val Ile Lys Ala Ala Lys
        195

<210> SEQ ID NO 34
<211> LENGTH: 200
<212> TYPE: PRT
<213> ORGANISM: Homo sapiens

<400> SEQUENCE: 34

Glu Val Ser Ile Glu Asp Ser Ala Gln Ser Asp Leu Lys Glu Val Met
1               5                   10                  15

Val Leu Asn Ala Thr Glu Ser Phe Val Tyr Glu Pro Lys Glu Gln Lys
            20                  25                  30

Lys Met Phe His Ala Thr Val Ala Thr Glu Asn Glu Val Phe Arg Val
        35                  40                  45

Lys Val Phe Asn Ile Asp Leu Lys Glu Lys Phe Thr Pro Lys Lys Ile
50                  55                  60

Ile Ala Ile Ala Asn Tyr Val Cys Arg Asn Gly Phe Leu Glu Val Tyr
65                  70                  75                  80

Pro Phe Thr Leu Val Ala Asp Val Asn Ala Asp Arg Asn Met Glu Ile
                85                  90                  95
```

```
Pro Lys Gly Leu Ile Arg Ser Ala Ser Val Thr Pro Lys Ile Asn Gln
            100                 105                 110

Leu Cys Ser Gln Thr Lys Gly Ser Phe Val Asn Gly Val Phe Glu Val
            115                 120                 125

His Lys Lys Asn Val Arg Gly Glu Phe Thr Tyr Tyr Glu Ile Gln Asp
            130                 135                 140

Asn Thr Gly Lys Met Glu Val Val His Gly Arg Leu Thr Thr Ile
145                 150                 155                 160

Asn Cys Glu Glu Gly Asp Lys Leu Lys Leu Thr Cys Phe Glu Leu Ala
                165                 170                 175

Pro Lys Ser Gly Asn Thr Gly Glu Leu Arg Ser Val Ile His Ser His
            180                 185                 190

Ile Lys Val Ile Lys Thr Arg Lys
            195                 200

<210> SEQ ID NO 35
<211> LENGTH: 198
<212> TYPE: PRT
<213> ORGANISM: Mus musculus

<400> SEQUENCE: 35

Glu Ser Phe Glu Gly Asp Gly Tyr His Lys Gly Pro Lys Gln Val Val
1               5                   10                  15

Ala Leu Lys Ala Thr Lys Leu Phe Thr Tyr Asp Ser Ile Lys Ser Lys
            20                  25                  30

Lys Met Phe His Ala Thr Val Ala Thr Asp Thr Glu Phe Phe Arg Val
            35                  40                  45

Met Val Phe Glu Glu Asn Leu Glu Lys Lys Phe Ile Pro Gly Asn Thr
        50                  55                  60

Ile Ala Leu Ser Asp Tyr Phe Gly Met Tyr Gly Ser Leu Ala Ile His
65                  70                  75                  80

Glu Tyr Ser Ser Val Ser Glu Val Lys Ser Gln Asn Lys Glu Asp Ser
                85                  90                  95

Ser Ser Ser Asp Glu Arg Pro Ile Glu His Leu Lys Ile Cys Asp Leu
            100                 105                 110

His Leu Gln Thr Glu Glu Arg Leu Val Asp Gly Glu Phe Lys Val Tyr
            115                 120                 125

Arg Lys Ser Ser Gly Asn Asn Cys Ile Cys Tyr Gly Ile Trp Asp Asp
            130                 135                 140

Thr Gly Ala Met Lys Val Val Ser Gly Gln Leu Thr Ser Val Asn
145                 150                 155                 160

Cys Glu Ile Gly Asn Thr Ile Arg Leu Val Cys Phe Glu Leu Thr Ser
                165                 170                 175

Asn Ala Asp Glu Trp Phe Leu Arg Ala Thr Arg Tyr Ser Tyr Met Glu
            180                 185                 190

Val Ile Met Pro Glu Lys
            195

<210> SEQ ID NO 36
<211> LENGTH: 199
<212> TYPE: PRT
<213> ORGANISM: Mus musculus
```

<400> SEQUENCE: 36

Glu Pro Ala Lys Glu Glu Asp His His His Gly Pro Lys Gln Val Met
1               5                   10                  15

Val Leu Lys Val Thr Glu Pro Phe Thr Tyr Asp Leu Lys Glu Asp Lys
            20                  25                  30

Arg Met Phe His Ala Thr Val Ala Thr Glu Thr Glu Phe Phe Arg Val
        35                  40                  45

Lys Val Phe Asp Thr Ala Leu Lys Ser Lys Phe Ile Pro Arg Asn Ile
    50                  55                  60

Ile Ala Ile Ser Asp Tyr Phe Gly Cys Asn Gly Phe Leu Glu Ile Tyr
65                  70                  75                  80

Arg Ala Ser Cys Val Ser Asp Val Asn Val Asn Pro Thr Met Val Ile
                85                  90                  95

Ser Asn Thr Leu Arg Gln Arg Ala Asn Ala Thr Pro Lys Ile Ser Tyr
            100                 105                 110

Leu Phe Ser Gln Ala Arg Gly Thr Phe Val Ser Gly Glu Tyr Leu Val
        115                 120                 125

Asn Lys Lys Thr Glu Arg Asn Lys Phe Ile Tyr Tyr Gly Ile Gly Asp
    130                 135                 140

Asp Thr Gly Lys Met Glu Val Val Val Tyr Gly Arg Leu Thr Asn Val
145                 150                 155                 160

Arg Cys Glu Pro Gly Ser Lys Leu Arg Leu Val Cys Phe Glu Leu Thr
                165                 170                 175

Ser Thr Glu Asp Gly Trp Gln Leu Arg Ser Val Arg His Ser Tyr Met
            180                 185                 190

Gln Val Ile Asn Ala Arg Lys
        195

<210> SEQ ID NO 37
<211> LENGTH: 201
<212> TYPE: PRT
<213> ORGANISM: Homo sapiens

<400> SEQUENCE: 37

Val Thr Pro Arg Arg Asn Val Leu Gln Lys Arg Pro Val Ile Val Lys
1               5                   10                  15

Val Leu Ser Thr Thr Lys Pro Phe Glu Tyr Glu Thr Pro Glu Met Glu
            20                  25                  30

Lys Lys Ile Met Phe His Ala Thr Val Ala Thr Gln Thr Gln Phe Phe
        35                  40                  45

His Val Lys Val Leu Asn Thr Ser Leu Lys Glu Lys Phe Asn Gly Lys
    50                  55                  60

Lys Ile Ile Ile Ile Ser Asp Tyr Leu Glu Tyr Asp Ser Leu Leu Glu
65                  70                  75                  80

Val Asn Glu Glu Ser Thr Val Ser Glu Ala Gly Pro Asn Gln Thr Phe
                85                  90                  95

Glu Val Pro Asn Lys Ile Ile Asn Arg Ala Lys Glu Thr Leu Lys Ile
            100                 105                 110

Asp Ile Leu His Lys Gln Ala Ser Gly Asn Ile Val Tyr Gly Val Phe
        115                 120                 125

Met Leu His Lys Lys Thr Val Asn Gln Lys Thr Thr Ile Tyr Glu Ile
    130                 135                 140

Gln Asp Asp Arg Gly Lys Met Asp Val Val Gly Thr Gly Gln Cys His
145                 150                 155                 160

Asn Ile Pro Cys Glu Glu Gly Asp Lys Leu Gln Leu Phe Cys Phe Arg
            165                 170                 175

Leu Arg Lys Lys Asn Gln Met Ser Lys Leu Ile Ser Glu Met His Ser
        180                 185                 190

Phe Ile Gln Ile Lys Lys Lys Thr Asn
        195                 200

<210> SEQ ID NO 38
<211> LENGTH: 198
<212> TYPE: PRT
<213> ORGANISM: Mus musculus

<400> SEQUENCE: 38

Asn Ile Ser Lys Gly Ala Val Leu His Glu Lys Pro Met Thr Val Met
1               5                   10                  15

Val Leu Thr Ala Thr Glu Pro Phe Asn Tyr Lys Glu Gly Lys Glu Asn
            20                  25                  30

Met Phe His Ala Thr Val Ala Thr Glu Ser Gln Tyr Tyr Arg Val Lys
        35                  40                  45

Val Phe Asn Met Asp Leu Lys Glu Lys Phe Thr Glu Asn Lys Phe Ile
    50                  55                  60

Thr Ile Ser Lys Tyr Phe Asn Ser Ser Gly Ile Leu Glu Ile Asn Glu
65                  70                  75                  80

Thr Ala Thr Val Ser Glu Ala Ala Pro Asn Gln Met Phe Glu Val Pro
                85                  90                  95

Lys Asn Ile Ile Arg Ser Ala Lys Glu Thr Leu Lys Ile Ser Lys Ile
            100                 105                 110

Lys Glu Leu Asp Ser Gly Thr Leu Ile Tyr Gly Val Phe Ala Val Glu
        115                 120                 125

Lys Lys Lys Val Asn Asp Lys Ser Ile Thr Phe Lys Ile Lys Asp Asn
    130                 135                 140

Glu Asp Asn Ile Lys Val Val Trp Asp Lys Glu Gln His Asn Ile Asn
145                 150                 155                 160

Tyr Glu Lys Gly Asp Lys Leu Gln Leu Phe Ser Phe His Leu Arg Lys
                165                 170                 175

Gly Asn Gly Lys Pro Ile Leu His Ser Gly Asn His Ser Phe Ile Lys
            180                 185                 190

Gly Glu Lys Leu Leu Lys
        195

<210> SEQ ID NO 39
<211> LENGTH: 201
<212> TYPE: PRT
<213> ORGANISM: Mus musculus

<400> SEQUENCE: 39

Asn Ile Pro Arg Gly Ala Val Leu His Ser Glu Pro Leu Thr Val Met
1               5                   10                  15

Val Leu Thr Ala Thr Asp Pro Phe Glu Tyr Glu Ser Pro Glu His Glu
            20                  25                  30

Val Lys Asn Met Leu His Ala Thr Val Ala Thr Val Ser Gln Tyr Phe
        35                  40                  45

His Val Lys Val Phe Asn Ile Asn Leu Lys Lys Phe Thr Lys Lys
    50                  55                  60

Asn Phe Ile Ile Ile Ser Asn Tyr Phe Glu Ser Lys Gly Ile Leu Glu
65                  70                  75                  80

```
Ile Asn Glu Thr Ser Ser Val Leu Glu Ala Ala Pro Asp Gln Met Ile
                85                  90                  95

Glu Val Pro Asn Ser Ile Ile Arg Asn Ala Asn Ala Ser Pro Lys Ile
            100                 105                 110

Cys Asp Ile Gln Lys Gly Thr Ser Gly Ala Val Phe Tyr Gly Val Phe
            115                 120                 125

Thr Leu His Lys Lys Thr Val Asn Arg Lys Asn Thr Ile Tyr Glu Ile
        130                 135                 140

Lys Asp Gly Ser Gly Ser Ile Glu Val Val Gly Ser Gly Lys Trp His
145                 150                 155                 160

Asn Ile Asn Cys Lys Glu Gly Asp Lys Leu His Leu Phe Cys Phe His
                165                 170                 175

Leu Lys Thr Ile Asp Arg Gln Pro Lys Leu Val Cys Gly Glu His Ser
            180                 185                 190

Phe Ile Lys Ile Ser Lys Arg Gly Asn
            195                 200
```

<210> SEQ ID NO 40
<211> LENGTH: 220
<212> TYPE: PRT
<213> ORGANISM: Homo sapiens

<400> SEQUENCE: 40

```
Pro Ile Ala Ser Leu Thr Pro Tyr Gln Ser Lys Trp Thr Ile Cys Ala
1               5                   10                  15

Arg Val Thr Asn Lys Ser Gln Ile Arg Thr Trp Ser Asn Ser Arg Gly
            20                  25                  30

Glu Gly Lys Leu Phe Ser Leu Glu Leu Val Asp Glu Ser Gly Glu Ile
        35                  40                  45

Arg Ala Thr Ala Phe Asn Glu Gln Val Asp Lys Phe Phe Pro Leu Ile
    50                  55                  60

Glu Val Asn Lys Val Tyr Tyr Phe Ser Lys Gly Thr Leu Lys Ile Ala
65                  70                  75                  80

Asn Lys Gln Phe Thr Ala Val Lys Asn Asp Tyr Glu Met Thr Phe Asn
                85                  90                  95

Asn Glu Thr Ser Val Met Pro Cys Glu Asp Asp His His Leu Pro Thr
            100                 105                 110

Val Gln Phe Asp Phe Thr Gly Ile Asp Asp Leu Glu Asn Lys Ser Lys
            115                 120                 125

Asp Ser Leu Val Asp Ile Ile Gly Ile Cys Lys Ser Tyr Glu Asp Ala
        130                 135                 140

Thr Lys Ile Thr Val Arg Ser Asn Asn Arg Glu Val Ala Lys Arg Asn
145                 150                 155                 160

Ile Tyr Leu Met Asp Thr Ser Gly Lys Val Val Thr Ala Thr Leu Trp
                165                 170                 175

Gly Glu Asp Ala Asp Lys Phe Asp Gly Ser Arg Gln Pro Val Leu Ala
            180                 185                 190

Ile Lys Gly Ala Arg Val Ser Asp Phe Gly Gly Arg Ser Leu Ser Val
        195                 200                 205

Leu Ser Ser Ser Thr Ile Ile Ala Asn Pro Asp Ile
    210                 215                 220
```